United States Patent
Wang et al.

(10) Patent No.: US 12,171,596 B2
(45) Date of Patent: Dec. 24, 2024

(54) IMAGING SYSTEMS AND METHODS

(71) Applicant: SHANGHAI UNITED IMAGING HEALTHCARE CO., LTD., Shanghai (CN)

(72) Inventors: Wenying Wang, Houston, TX (US); Tao Feng, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 309 days.

(21) Appl. No.: 17/661,549

(22) Filed: Apr. 29, 2022

(65) Prior Publication Data
US 2023/0073283 A1    Mar. 9, 2023

Related U.S. Application Data

(63) Continuation-in-part of application No. 17/446,969, filed on Sep. 5, 2021, now Pat. No. 11,857,357.

(51) Int. Cl.
*A61B 6/03* (2006.01)
*A61B 6/00* (2024.01)
*A61B 6/06* (2006.01)
*G01T 1/29* (2006.01)

(52) U.S. Cl.
CPC .............. *A61B 6/037* (2013.01); *A61B 6/06* (2013.01); *A61B 6/5235* (2013.01); *G01T 1/2985* (2013.01)

(58) Field of Classification Search
CPC ......... A61B 6/037; A61B 6/06; A61B 6/5235; G01T 1/2985; G01T 1/1648
See application file for complete search history.

(56) References Cited

U.S. PATENT DOCUMENTS

| | | | |
|---|---|---|---|
| 5,512,754 A | 4/1996 | Enos | |
| 5,638,817 A | 6/1997 | Morgan et al. | |
| 7,498,580 B2 | 3/2009 | Lackas et al. | |
| 8,884,235 B2 | 11/2014 | Heukensfeldt Jansen et al. | |
| 2006/0065840 A1 | 3/2006 | Joung et al. | |
| 2007/0183642 A1 | 8/2007 | Ye et al. | |
| 2008/0116386 A1 | 5/2008 | Wagenaar et al. | |
| 2008/0237472 A1* | 10/2008 | Uribe ..................... A61B 6/037 250/363.1 | |

(Continued)

OTHER PUBLICATIONS

Inayatullah Shah Sayed et al. Effects of Unconventional (Material) Filters on the Quality of Images Produced by Three Gamma Camera Systems in Tc-99m SPECT, International Journal of Healthcare Sciences, 4(1): 203-209, 2016.

*Primary Examiner* — David P Porta
*Assistant Examiner* — Casey Bryant
(74) *Attorney, Agent, or Firm* — METIS IP LLC

(57) ABSTRACT

The present disclosure may provide a SPECT system. The SPECT system may include a collimator including a group of first pinholes and a group of second pinholes. The group of first pinholes may be configured to remain open. The group of second pinholes may be configured to alternate between an open configuration and a blocked configuration. The collimator may be configured to allow photons to traverse through at least one group of the group of first pinholes or the group of second pinholes. The SPECT system may also include a detector configured to detect at least a portion of the photons that have traversed the collimator.

20 Claims, 11 Drawing Sheets

(56) References Cited

U.S. PATENT DOCUMENTS

| | | |
|---|---|---|
| 2012/0305812 A1 | 12/2012 | Bowen et al. |
| 2020/0146641 A1* | 5/2020 | Mu .......................... A61B 6/06 |
| 2022/0133246 A1* | 5/2022 | Beekman .............. G01T 1/2985 |
| | | 378/4 |
| 2023/0072958 A1* | 3/2023 | Wang .................... G01T 1/1642 |
| 2023/0073283 A1* | 3/2023 | Wang ..................... A61B 6/037 |

* cited by examiner

IMAGING SYSTEMS AND METHODS

CROSS-REFERENCE TO THE RELATED APPLICATIONS

This application is a partial continuation of U.S. patent application Ser. No. 17/446,969 filed on Sep. 5, 2021, the contents of which are hereby incorporated by reference.

TECHNICAL FIELD

The disclosure generally relates to medical technology, and more particularly relates to imaging systems and methods.

BACKGROUND

Nuclear medicine functional imaging techniques (e.g., single-photon emission computed tomography (SPECT)) are widely used in medical diagnosis. For example, a radioactive tracer may be injected into an object to be examined, and then imaging data of the object may be acquired by scanning the object using a nuclear medicine imaging device. In some cases, the sensitivity of the nuclear medicine imaging device may be relatively low; that is, a relatively low percentage of photons emitted by the object may be detected, and a utilization rate of the photons may be relatively low, which in turn may negatively affect the quality of an image generated based on the imaging data. Therefore, it is desirable to provide imaging systems and methods with improved sensitivity.

SUMMARY

According to one aspect of the present disclosure, a single-photon emission computed tomography (SPECT) system may be provided. The SPECT system may include a collimator including a group of first pinholes and a group of second pinholes. The group of first pinholes may be configured to remain open. The group of second pinholes may be configured to alternate between an open configuration and a blocked configuration. The collimator may be configured to allow photons to traverse through at least one group of the group of first pinholes or the group of second pinholes. The SPECT system may also include a detector configured to detect at least a portion of the photons that have traversed the collimator.

In some embodiments, the SPECT system may include a plurality of filters. Each of the plurality of filters may correspond to at least one second pinhole of the group of second pinholes.

In some embodiments, for each of the plurality of filters, the filter may be movable between a first position and a second position. When the filter is at the first position, at least one second pinhole of the group of second pinholes corresponding to the filter may be at its open configuration; when the filter is at the second position, the at least one second pinhole corresponding to the filter may be at its blocked configuration.

In some embodiments, the plurality of filters may be located on a rotatable ring.

In some embodiments, the group of second pinholes may be configured to allow a first portion of the photons to traverse at the open configuration and a second portion of the photons to traverse at the blocked configuration. A ratio of the second portion to the first portion may be smaller than a ratio threshold.

In some embodiments, the ratio may relate to a thickness of each of the plurality of filters.

In some embodiments, the plurality of filters may be made of a heavy metal.

In some embodiments, the heavy metal may include at least one of tungsten, gold, copper, lead, or an alloy thereof.

In some embodiments, the group of second pinholes may be at the blocked configuration during a first time period and at the open configuration during a second time period. The second time period may be longer than the first time period.

In some embodiments, a switch from the blocked configuration to the open configuration of the group of second pinholes may take a third time period.

In some embodiments, the third time period may be smaller than at least one of the first time period or the second time period.

In some embodiments, a total duration of the first time period, the second time period, and the third time period may be smaller than a time threshold.

In some embodiments, photons that traverse the collimator through each first pinhole of the group of first pinholes may correspond to a first projection region. The first projection regions may be non-overlapping.

In some embodiments, photons that traverse the collimator through each second pinhole of the group of second pinholes may correspond to a second projection region. The second projection regions may be non-overlapping.

In some embodiments, at least one of the first projection regions may overlap at least one of the second projection regions.

In some embodiments, at least one of the first projection regions may overlap at least two of the second projection regions; or at least one of the second projection regions may overlap at least two of the first projection regions.

In some embodiments, the group of first pinholes and the group of second pinholes may be alternately positioned such that each first pinhole is positioned between two neighboring second pinholes.

According to another aspect of the present disclosure, a system may be provided. The system may include a single-photon emission computed tomography (SPECT) device. The SPECT device may include a collimator having a group of first pinholes and a group of second pinholes. The group of first pinholes may be configured to remain open. The group of second pinholes may be configured to alternate between an open configuration and a blocked configuration. The system may also include at least one storage device storing executable instructions for single-photon emission computed tomography (SPECT) imaging and at least one processor in communication with the at least one storage device, wherein when executing the executable instructions, the at least one processor may be configured to cause the system to perform operations including: causing the group of second pinholes to maintain at the blocked configuration during a first time period; acquiring a first projection data set during the first time period; causing the group of second pinholes to maintain at the open configuration during a second time period; acquiring a second projection data set during the second time period; and generating an image based on the first projection data set and the second projection data set.

In some embodiments, the second projection data set may include a first portion that corresponds to photons traversing the collimator through the group of second pinholes at the open configuration and a second portion that corresponds photons traversing the collimator through the group of first pinholes. The generating an image based on the first projection data set and the second projection data set may include: determining the first portion of the second projection data set based on the first projection data set and the second projection data set, and generating the image based on the first projection data set and the first portion of the second projection data.

According to another aspect of the present disclosure, a collimator for single-photon emission computed tomography (SPECT) imaging may be provided. The collimator may include a group of first pinholes and a group of second pinholes. The group of first pinholes may be configured to remain open. The group of second pinholes may be configured to alternate between an open configuration and a blocked configuration. The collimator may be configured to allow photons to traverse through at least one group of the group of first pinholes or the group of second pinholes.

According to another aspect of the present disclosure, a single-photon emission computed tomography (SPECT) system may be provided. The SPECT system may include a collimator and a detector. The collimator may include a group of first pinholes and a group of second pinholes. The group of first pinholes may be configured to alternate between an open configuration and a blocked configuration. The group of second pinholes may be configured to alternate between an open configuration and a blocked configuration. The collimator may be configured to allow photons to traverse through at least one group of the group of first pinholes or the group of second pinholes. The detector may be configured to detect at least a portion of the photons that have traversed the collimator. The group of first pinholes and the group of second pinholes may be configured to implement one of a plurality of pinhole modes including: a first pinhole mode in which the group of first pinholes are configured at the blocked configuration, while the group of second pinholes are configured at the open configuration; a second pinhole mode in which the group of first pinholes and the group of second pinholes are both configured at the open configuration; or a third pinhole mode in which the group of first pinholes are configured at the open configuration, while the group of second pinholes are configured at the blocked configuration.

In some embodiments, the SPECT system may include a plurality of filters. Each of plurality of filters may correspond to at least one first pinhole of the group of first pinholes and at least one second pinhole of the group of second pinholes.

In some embodiments, for each of the plurality of filters, the filter may be movable between a first position, a second position, and a third position. When the filters are at their respective first positions, the group of first pinholes and the group of second pinholes may be at the first pinhole mode. When the filters are at their respective second positions, the group of first pinholes and the group of second pinholes may be at the second pinhole mode. When the filter is at their respective third positions, the group of first pinholes and the group of second pinholes may be at the third pinhole mode.

In some embodiments, the group of first pinholes may be configured to allow a first portion of the photons to traverse at the open configuration and a second portion of the photons to traverse at the blocked configuration. A ratio of the second portion to the first portion may be smaller than a ratio threshold.

In some embodiments, the group of second pinholes may be configured to allow a first portion of the photons to traverse at the open configuration and a second portion of the photons to traverse at the blocked configuration. A ratio of the second portion to the first portion may be smaller than a ratio threshold.

According to another aspect of the present disclosure, a system may be provided. The system may include a single-photon emission computed tomography (SPECT) device. The SPECT device may include a collimator having a group of first pinholes and a group of second pinholes. The group of first pinholes may be configured to alternate between an open configuration and a blocked configuration. The group of second pinholes may be configured to alternate between an open configuration and a blocked configuration. The system may include at least one storage device storing executable instructions for single-photon emission computed tomography (SPECT) imaging; and at least one processor in communication with the at least one storage device, wherein when executing the executable instructions, the at least one processor may be configured to cause the system to perform operations including: causing the group of first pinholes to maintain at the blocked configuration and the group of second pinholes to maintain at the open configuration during a first time period; acquiring a first projection data set during the first time period; causing the group of first pinholes to maintain at the open configuration and the group of second pinholes to maintain at the blocked configuration during a second time period; acquiring a second projection data set during the second time period; causing both the group of first pinholes and the group of second pinholes to maintain at the open configuration during a third time period; acquiring a third projection data set during the third time period; and generating an image based on the first projection data set, the second projection data set, and the third projection data set.

In some embodiments, the third projection data set may include a first portion that corresponds to photons traversing the collimator through the group of second pinholes at the open configuration and a second portion that corresponds photons traversing the collimator through the group of first pinholes at the open configuration. The generating an image based on the first projection data set, the second projection data set, and the third projection data set may include: separating the first portion of the third projection data set and the second portion of the third projection data set based on the first projection data set, the second projection data set, and the third projection data set, and generating the image based on at least one of the first projection data set, the second projection date set, the first portion of the third projection data set, or the second portion of the third projection data set.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein.

DETAILED DESCRIPTION

Figure 1:
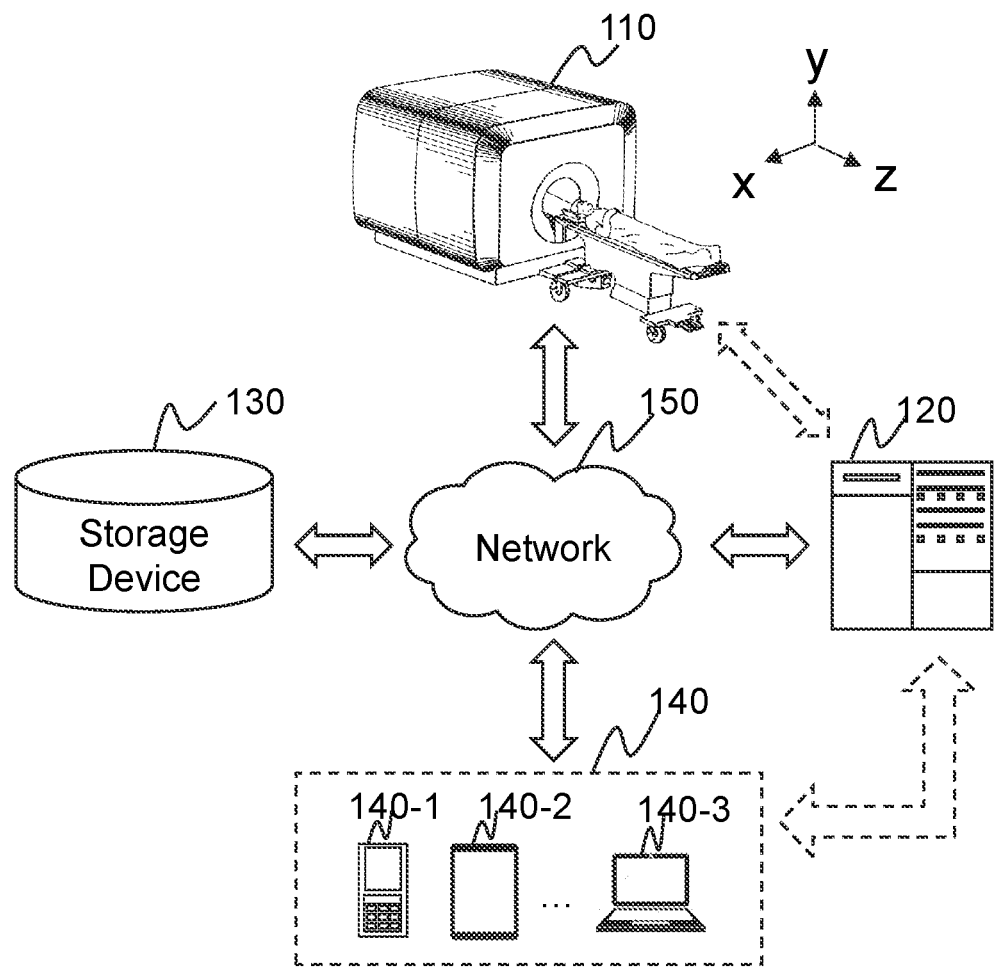
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

According to one aspect of the present disclosure, an imaging system may be provided. The imaging system may include a detector and a collimator. The collimator may include a group of first pinholes and a group of second pinholes. The collimator may be configured to allow photons to traverse the collimator through at least one group of the group of first pinholes or the group of second pinholes. The detector may be configured to detect at least a portion of the photons that have traversed the collimator.

In some embodiments, the group of first pinholes may be configured to remain open. The group of second pinholes may be configured to alternate between an open configuration and a blocked configuration. Such a second pinhole may also be referred to as a multiplexing pinhole. When the group of second pinholes are at the open configuration, the photons may traverse the collimator both through the group of first pinholes and the group of second pinholes. When the group of second pinholes are at the blocked configuration, the photons may mainly traverse the collimator through the group of first pinholes and (substantially) no photons traverse through the group of second pinholes.

In some embodiments, the group of second pinholes may be at the blocked configuration during a first time period. A first projection data set may be acquired during the first time period. The group of second pinholes may be at the open configuration during a second time period. A second projection data set may be acquired during the second time period. An image may be generated based on the first projection data set and the second projection data set. In some embodiments, the second projection data set may include a first portion that corresponds to photons traversing the collimator through the group of second pinholes at the open configuration and a second portion that corresponds to photons traversing the collimator through the group of first pinholes.

Since the photons may mainly traverse the collimator through the group of first pinholes and (substantially) no photons traverse the collimator through the group of second pinholes at the blocked configuration, the effect of the photons that traverse the collimator through the group of second pinholes at the blocked configuration on the first projection data set may be negligible. The first projection data set may be considered to be generated only based on the photons that traverse the collimator through the group of first pinholes during the first time period. Therefore, the first portion of the second projection data set may be estimated based on the first projection data set and the second projection data set. The image may be generated based on at least one of the first projection data set, the first portion of the second projection data set, or the second portion of the second projection data set.

In some embodiments, photons that traverse the collimator through each first pinhole of the group of first pinholes may correspond to a first projection region. The first projection regions corresponding to the group of first pinholes may be non-overlapping. Photons that traverse the collimator through each second pinhole of the group of second pinholes may correspond to a second projection region. The second projection regions corresponding to the group of second pinholes may be non-overlapping. In some embodiments, at least one of the first projection regions may at least partially overlap at least one of the second projection regions. Therefore, when the group of second pinholes are at the open configuration, a portion of the detector corresponding to each overlapping region may detect photons that traverse the collimator through at least one first pinhole corresponding to the overlapping region and photons that traverse the collimator through at least one second pinhole corresponding to the overlapping region. In such cases, the second projection data set that includes projection data corresponding to both photons traversing through the at least one first pinhole and photons traversing through the at least one second pinhole may be denoted as a multiplexing projection data set.

By causing the group of second pinholes to alternate between the blocked configuration and the open configuration in different time periods and decomposing the first portion of the second projection data set corresponding to the group of second pinholes from the second projection dataset as illustrated above, multiplexing artifacts caused by the multiplexing projection data set may be reduced. Besides, compared to an existing collimator that includes only a group of first pinholes that remain open, angular sampling of the imaging system may be improved, thereby increasing the sensitivity of the imaging system, and further improving the quality of the image. Taking FIG. 8 as an example, an area formed by the curve and the coordinate axis may indicate the increment of the sensitivity of the imaging system.

FIG. 1 is a schematic diagram illustrating an exemplary imaging system according to some embodiments of the present disclosure.

As illustrated in FIG. 1, the imaging system 100 may include an imaging device 110, a processing device 120, a storage device 130, one or more terminal devices 140, and a network 150. The components in the imaging system 100 may be connected in one or more of various ways. Merely by way of example, the imaging device 110 may be connected to the processing device 120 through the network 150. As another example, the imaging device 110 may be connected to the processing device 120 directly as illustrated in FIG. 1. As a further example, the terminal device 140 may be connected to another component of the imaging system 100 (e.g., the processing device 120) via the network 150. As still a further example, the terminal device 140 may be connected to the processing device 120 directly as illustrated by the dotted arrow in FIG. 1. As still a further example, the storage device 130 may be connected to another component of the imaging system 100 (e.g., the processing device 120) directly as illustrated in FIG. 1, or through the network 150.

The imaging device 110 may be configured to acquire imaging data relating to at least one part of an object. For example, the imaging device 110 may scan an object or a portion thereof that is located within its detection region (also referred to as "a field of view") (e.g., 280 in FIGS. 2A and 2B, 980 in FIGS. 9A-9C) and generate imaging data relating to the object or the portion thereof. The imaging data relating to at least one part of the object may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. The object may be biological or non-biological. For example, the object may include a patient, an animal, a man-made object (e.g., a phantom), etc. As another example, the object may include a specific portion, organ, and/or tissue of the patient. For example, the object may include the head, the neck, the thorax, the heart, the stomach, a blood vessel, soft tissue, a tumor, nodules, or the like, or any combination thereof. In some embodiments, the imaging device 110 may include a single modality imaging device. For example, the imaging device 110 may include a single-photon emission computed tomography (SPECT) device. In some embodiments, the imaging device 110 may include a multi-modality imaging device. Exemplary multi-modality imaging devices may include a SPECT-CT device, a SPECT-PET device, a SPECT-MR device, etc.

In some embodiments, a radioactive tracer may be injected into the object, and then the imaging data may be acquired by scanning the object using the imaging device 110 (e.g., the SPECT device). For example, the object may be scanned by the imaging device 110 in a predetermined time period after the radioactive tracer is injected into the object. As another example, the object may be scanned by the imaging device 110 in a certain time period after a distribution of the radioactive tracer in the object reaches equilibrium or steady-state. In some embodiments, the radioactive tracer may include technetium-99 (Tc-99), fluorine-18 (F-18), indium-111 (In-111), iodine-131 (I-131), or the like, or any combination thereof.

In some embodiments, the imaging device 110 (e.g., the SPECT device) may include a gantry, a collimator, a detector, an electronics module, etc. The gantry may support one or more parts of the imaging device 110, for example, the collimator, the detector, the electronics module, etc. The collimator may be configured to collimate photons (e.g., γ photons) emitted from the object after injecting the radioactive tracer. The detector may be configured to detect at least a portion of the photons collimated by the collimator and/or generate electrical signals (e.g., scintillation pulses). The electronics module may be configured to convert the electrical signals to digital signals to generate the imaging data. In some embodiments, the electronics module may be part of the detector.

In some embodiments, the collimator may be plate-shaped, ring-shaped, etc. The detector may be plate-shaped, ring-shaped, etc. In some embodiments, each of the collimator and the detector may be ring-shaped. For example, the detector and the collimator may be arranged concentrically. In some embodiments, each of the collimator and the detector may be plate-shaped. In some embodiments, one of the collimator and the detector may be ring-shaped, and the other of the collimator and the detector may be plate-shaped. It should be noted that a count of the plate-shaped collimator or a count of the plate-shaped detector may be, for example, 1, 2, 3, or more. In some embodiments, at least one of the collimator or the detector may be stationary with respect to a fixed portion of the imaging device 110. In some embodiments, at least one of the collimator or the detector may be rotatable with respect to a fixed portion of the imaging device 110.

The processing device 120 may process data and/or information obtained from the imaging device 110, the terminal device 140, and/or the storage device 130. For example, the processing device 120 may obtain imaging data acquired by the imaging device 110. The processing device 120 may generate an image based on the imaging data. In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the imaging device 110, the terminal device 140, and/or the storage device 130 via the network 150. As another example, the processing device 120 may be directly connected to the imaging device 110, the terminal device 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data (e.g., imaging data) obtained from the terminal device 140 and/or the processing device 120. In some embodiments, the storage device 130 may store data and/or instructions that the processing device 120 may execute or use to perform exemplary methods/systems described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform.

In some embodiments, the storage device 130 may be connected to the network 150 to communicate with one or more other components in the imaging system 100 (e.g., the processing device 120, the terminal device 140). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal device 140, etc.). In some embodiments, the storage device 130 may be part of the processing device 120.

The terminal device 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 140 may be part of the processing device 120.

The network 150 may include any suitable network that can facilitate the exchange of information and/or data for the imaging system 100. In some embodiments, one or more components of the imaging device 110, the terminal device 140, the processing device 120, the storage device 130, etc., may communicate information and/or data with one or more other components of the imaging system 100 via the network 150. For example, the processing device 120 may obtain data from the imaging device 110 via the network 150. As another example, the processing device 120 may obtain user instructions from the terminal device 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

In the present disclosure, the X-axis, the Y-axis, and the Z-axis shown in FIG. 1 may form an orthogonal coordinate system. The X-axis and the Z-axis shown in FIG. 1 may be horizontal, and the Y-axis may be vertical. As illustrated, the positive X-direction along the X-axis may be from the right side to the left side of the imaging device 110 seen from the direction facing the front of the imaging device 110; the positive Y-direction along the Y-axis shown in FIG. 1 may be from the lower part to the upper part of the imaging device 110; the positive Z-direction along the Z-axis shown in FIG. 1 may refer to a direction in which the object is moved out of a detection region (or referred to as the bore) of the imaging device 110.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios.

In some embodiments of the present disclosure, the imaging device 110 of the imaging system 100 may include a collimator and a detector. The collimator may include a group of first pinholes and a group of second pinholes. The collimator may be configured to allow photons to traverse the collimator through at least one group of the group of first pinholes or the group of second pinholes. The detector may be configured to detect at least a portion of the photons that have traversed the collimator. As described above, the photons may be emitted by an object (e.g., a patient) after a radioactive tracer is injected into the object.

In some embodiments, the group of first pinholes may be configured to remain open. The group of first pinholes may be configured to allow a portion of the photons to traverse. The group of second pinholes may be configured to alternate between an open configuration and a blocked configuration. In some embodiments, the group of second pinholes may be configured to allow a first portion of the photons to traverse at the open configuration and a second portion of the photons to traverse at the blocked configuration. In some embodiments, a ratio (also referred to as "a first transmission ratio" below) of the second portion to the first portion may be smaller than a ratio threshold (e.g., 0.0001, 0.001, 0.01), that is, (substantially) no photons traverse the collimator through the group of second pinholes at the blocked configuration. In some embodiments, the ratio of the second portion to the first portion may be zero, that is, no photons traverse the collimator through the group of second pinholes at the blocked configuration.

In some embodiments, the imaging device 110 may include a plurality of filters. The plurality of filters may be configured to facilitate the group of second pinholes to switch between the open configuration and the blocked configuration. As used herein, the open configuration of a second pinhole may include a configuration in which the second pinhole is fully open to allow photons to pass through or a configuration in which the second pinhole is partially open and partially blocked such that only a portion of the second pinhole is available for photons to pass through. The extent to which a second pinhole is open may be assessed in terms of a transmission ratio. A transmission ratio of a second pinhole at a certain configuration may be determined by a ratio of the maximum amount of photons allowed to pass through the second pinhole at the certain configuration to the amount of photons allowed to pass through the second pinhole when the second pinhole is fully open. For instance, the transmission ratio of a second pinhole when it is fully open is (substantially) 1. As another example, the transmission ratio of a second pinhole when it is fully open is below 1. As used herein, the blocked configuration of a second pinhole may include a configuration in which the second pinhole is completely blocked such that (substantially) no photons may pass through the second pinhole or that the transmission ratio of the second pinhole under the blocked configuration is (substantially) zero. As used herein, substantially, when used to describe a feature, may indicate that the deviation from the feature is below a threshold. For instance, that the transmission ratio of the second pinhole under the blocked configuration is substantially zero may indicate that the transmission ratio of the second pinhole under the blocked configuration may be no more than 5%, 10%, etc. As another example, that the transmission ratio of the second pinhole under the open configuration is substantially 1 may indicate that the transmission ratio of the second pinhole under the open configuration may be no less than 95%, 90%, etc.

In some embodiments, each of the plurality of filters may correspond to at least one second pinhole of the group of second pinholes such that the movement of the filter may facilitate the corresponding at least one second pinhole to switch between the open configuration and the blocked configuration. For example, each of the plurality of filters may correspond to one of the group of second pinholes (e.g., as illustrated in FIGS. 2A-3B) such that the movement of the filter may facilitate the corresponding second pinhole to switch between the open configuration and the blocked configuration. As another example, each of the plurality of filters may correspond to two or more of the group of second pinholes such that the movement of the filter may facilitate each of the corresponding two or more second pinholes to switch between the open configuration and the blocked configuration.

In some embodiments, the plurality of filters may be movable. In some embodiments, each of the plurality of filters may be moved out of a photon pathway through at least one second pinhole corresponding to the filter such that photons (also referred to as "second photons") may traverse the collimator through the at least one second pinhole. In some embodiments, the filter may be moved to block at least a part of the photon pathway through at least one second pinhole corresponding to the filter such that (substantially) no or only a portion of the second photons may traverse the collimator through the at least one second pinhole. The transmission ratio of a second pinhole may change when the corresponding filter is at different positions.

In some embodiments, each of the plurality of filters may be movable between a first position and a second position. When the filter is at the first position, the filter may be positioned out of a photon pathway through at least one second pinhole corresponding to the filter, and the at least one corresponding second pinhole may be at the open configuration. Accordingly, a transmission ratio (also referred to as a second transmission ratio) corresponding to the at least one corresponding second pinhole at the open configuration may be equal to or less than 1.

In some embodiments, when the filter is at the second position, the filter may be configured to (substantially) block the photon pathway of the at least one corresponding second pinhole such that the at least one corresponding second pinhole may be at the blocked configuration. A transmission ratio (also referred to as a first transmission ratio) corresponding to the at least one corresponding second pinhole at the blocked configuration may be (substantially) zero, e.g., smaller than a ratio threshold (e.g., 0.00001, 0.0001, 0.001). For example, the first transmission ratio may be zero, that is, no photons may traverse the collimator through the at least one corresponding second pinhole.

Figure 2A:
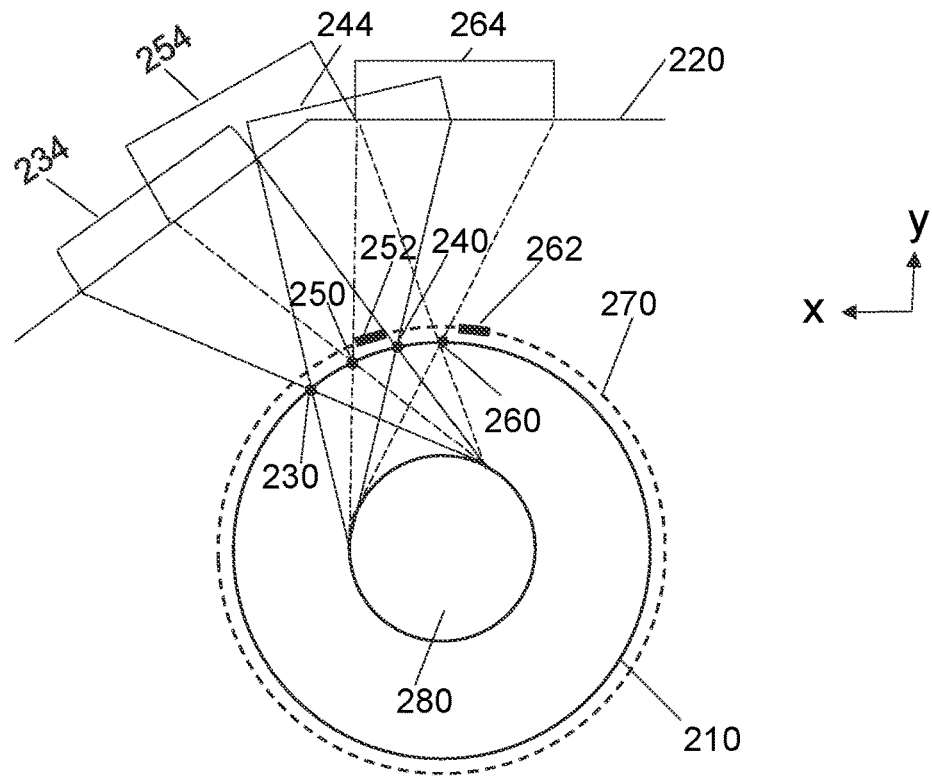
FIG. 2A illustrates exemplary second pinholes at an open configuration according to some embodiments of the present disclosure.
Figure 2B:
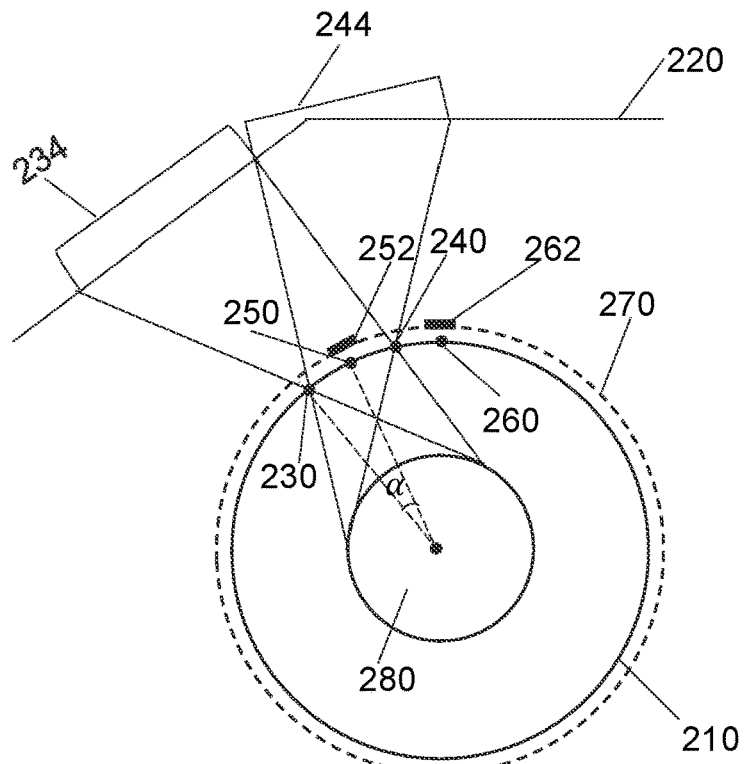
FIG. 2B illustrates exemplary second pinholes at a blocked configuration according to some embodiments of the present disclosure.

Taking the imaging device 200 in FIG. 2A and FIG. 2B as an example, a filter 252 may correspond to a second pinhole 250. A filter 262 may correspond to a second pinhole 260. The second pinholes 250 and 260 may be at the open configuration when the filters 252 and 262 are positioned as FIG. 2A. The second pinholes 250 and 260 may be at the blocked configuration when the filters 252 and 262 are positioned as FIG. 2B.

In some embodiments, the first transmission ratio of a second pinhole may relate to at least one parameter of a corresponding filter including, e.g., a thickness of the filter, a material of the filter, or the like, or a combination thereof. As used herein, the thickness of a filter may refer to a dimension of the filter along an emitting direction of at least a portion of photons that impinge on the filter. In some embodiments, each filter of some or all of the plurality of filters may have a same thickness. In some embodiments, the thickness of the filter may be large enough such that (substantially) no photons traverse the collimator through the group of second pinholes at the blocked configuration. For example, the thickness of the filter may be within a range, for example, 1 millimeter-10 millimeters, 2 millimeters-8 millimeters, 3 millimeters-5 millimeters, etc.

In some embodiments, for a filter of a certain thickness, the lower an attenuation coefficient of a material of a filter is, the fewer photons may be blocked by the filter. In some embodiments, for a filter of a certain thickness, the lower atomic number of the material of the filter is, the fewer photons may be blocked by the filter. In some embodiments, the atomic number of the material of the filter may exceed a threshold. In some embodiments, the material of each filter of some or all of the plurality of filters may be the same or different. In some embodiments, the material of some or all of the plurality of filters may be made of a heavy metal, for example, tungsten, gold, copper, lead, or an alloy thereof. For example, a filter may be made of tungsten with a thickness of 4 millimeters.

In some embodiments, the plurality of filters may be located on a rotatable ring (e.g., a ring 270 in FIG. 2A and FIG. 2B). When the rotatable ring is rotated to a third position (e.g., as illustrated in FIG. 2A), all of the plurality of filters may be at the first position, that is, all second pinholes of the group of second pinholes are at the open configuration. When the rotatable ring is rotated to a fourth position (e.g., as illustrated in FIG. 2B), all of the plurality of filters may be at the second position, that is, all of the group of second pinholes are at the blocked configuration.

Figure 3A:
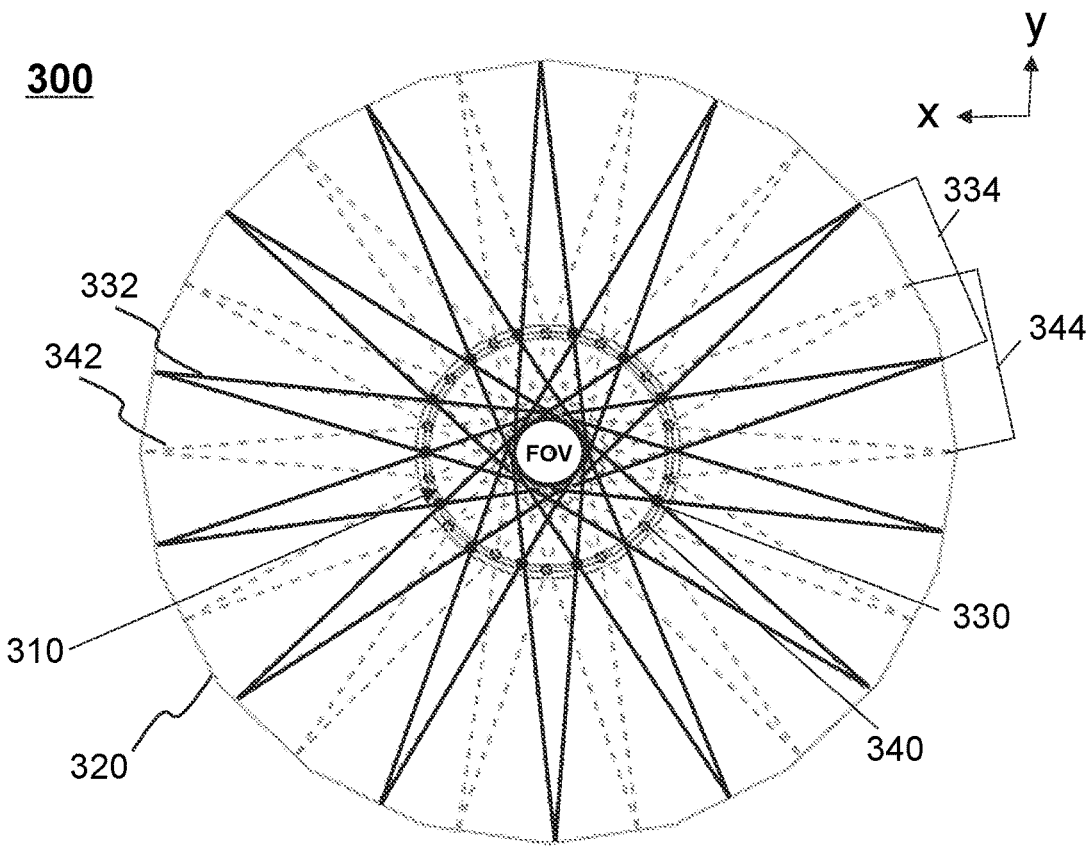
FIG. 3A and FIG. 3B are section views illustrating a portion of an exemplary imaging device according to some embodiments of the present disclosure.
Figure 3B:
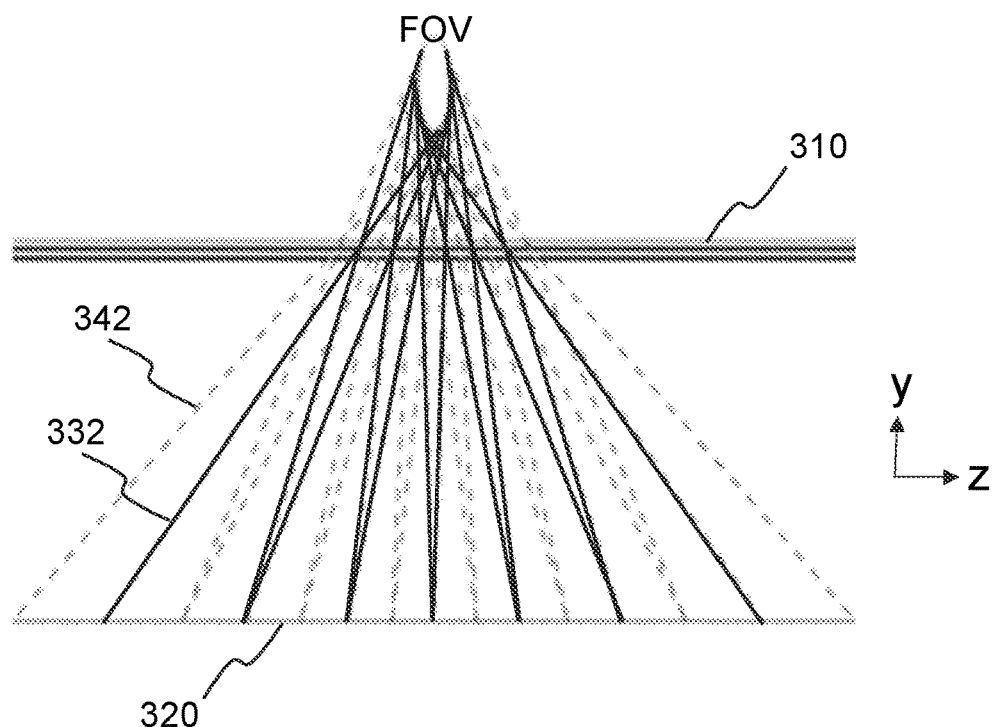

In some embodiments, at least two of the detector, the collimator, or the rotatable ring may be arranged concentrically. For example, the detector and the collimator may be arranged concentrically (e.g., as illustrated in FIG. 3A and FIG. 3B). As another example, the collimator and the rotatable ring may be arranged concentrically (e.g., as illustrated in FIG. 2A and FIG. 2B). As a further example, the detector, the collimator, and the rotatable ring may be configured concentrically. As used herein, "concentrically" indicates that central points (e.g., rotation centers, centers of gravity, centers of mass) of different components (e.g., the detector, the collimator, and the rotatably ring) may (substantially) coincide. As used herein, "substantially" indicates that a distance between two central points is below a threshold, e.g., 1 millimeter, 2 millimeters, 3 millimeters, etc.

In some embodiments, photons (also referred to as "first photons") that traverse the collimator through a first pinhole of the group of first pinholes may correspond to a first projection region. The first projection region of a corresponding first pinhole may refer to a region where at least a portion of the first photons impinge on the detector after traversing the collimator through the first pinhole. In some embodiments, the first projection regions corresponding to the group of first pinholes may be non-overlapping. In such cases, photons traversing through different first pinholes may impinge on different regions of the detector. Taking first pinholes 230 and 240 in FIG. 2A and FIG. 2B as an example, photons that traverse a collimator 210 through the first pinhole 230 may impinge on a first projection region 234 of a detector 220. Photons that traverse the collimator 210 through the first pinhole 240 may impinge on a first projection region 244 of the detector 220. The first projection region 234 may not overlap the first projection region 244. The first projection region 234 may be adjacent to the first projection region 244. In some embodiments, the aggregate of the first projection regions may cover the entire detector (e.g., as shown in FIG. 3A and FIG. 3B).

In some embodiments, photons (also referred to as "second photons") that traverse the collimator through a second pinhole of the group of second pinholes may correspond to a second projection region. The second projection region corresponding to a second pinhole may refer to a region where at least a portion of the second photons impinge on the detector after traversing the collimator through the second pinhole. In some embodiments, the second projection regions corresponding to the group of second pinholes may be non-overlapping. In such cases, photons traversing through different second pinholes may impinge on different regions of the detector. Taking second pinholes 250 and 260 in FIG. 2A as an example, photons that traverse the collimator 210 through the second pinhole 250 may impinge on a second projection region 254 of the detector 220. Photons that traverse the collimator 210 through the second pinhole 260 may impinge on a second projection region 264 of the detector 220. The second projection region 254 may not overlap the second projection region 264. The second projection region 254 may be adjacent to the second projection region 264. In some embodiments, the aggregate of the second projection regions may cover the entire detector (e.g., as shown in FIG. 3A and FIG. 3B).

In some embodiments, at least one of the first projection regions may at least partially overlap at least one of the second projection regions. The portion of the detector corresponding to an overlapping region between a first projection region and a second projection region may detect both photons traversing the first pinhole corresponding to the first projection region and photons traversing the second pinhole corresponding to the second projection region. In some embodiments, at least one of the first projection regions may at least partially overlap at least two of the second projection regions. In some embodiments, at least one of the second projection regions may at least partially overlap at least two of the first projection regions. Taking the first pinhole 230, the first pinhole 240, the second pinhole 250, and the second pinhole 260 in FIG. 2A as an example, the first projection region 234 corresponding to the first pinhole 230 and the first projection region 244 corresponding to the first pinhole 240 may each partially overlap the second projection region 254 corresponding to the second pinhole 250. The second projection region 254 and the second projection region 264 corresponding to the second pinhole 260 may each partially overlap the first projection region 244.

In some embodiments, the group of first pinholes may be circumferentially positioned or distributed on a surface of the collimator. In some embodiments, a photon count of photons traversing the collimator through the group of first pinholes may relate to at least one parameter including a size of each of the group of first pinholes, a pinhole count of the group of first pinholes, a shape of each of the group of first pinholes, etc. In some embodiments, the size (e.g., a length, a width, an area) of each first pinhole may be the same or different. In some embodiments, the pinhole count of the group of first pinholes may be, e.g., 12, 14, 15, 16, 17, 18, 20, etc. In some embodiments, a shape of each first pinhole may be the same or different. For example, a first pinhole may have a circular shape, a funnel shape, a "V" shape, a double conical shape, or the like, or any combination thereof.

In some embodiments, similar to the group of first pinholes, the group of second pinholes may be circumferentially positioned or distributed on the surface of the collimator. In some embodiments, a photon count of photons traversing the collimator through the group of second pinholes at the open configuration may relate to at least one parameter including a size of each of the group of second pinholes, a pinhole count of the group of second pinholes, a shape of each of the group of second pinholes, the extent to which each of the group of second pinholes is open (e.g., fully open, partially open), etc. In some embodiments, the size (e.g., a length, a width, an area) of each second pinhole may be the same or different. In some embodiments, the pinhole count of the group of second pinholes may be, e.g., 12, 14, 15, 16, 17, 18, 20, etc. In some embodiments, a shape of each second pinhole may be the same or different. For example, the second pinhole may have a circular shape, a funnel shape, a "V" shape, a double conical shape, or the like, or any combination thereof.

In some embodiments, the group of first pinholes and the group of second pinholes may be alternately positioned such that each first pinhole is positioned between two neighboring second pinholes and/or each second pinhole is positioned between two neighboring first pinholes. As used herein, two pinholes of a type is considered neighboring each other when there are no other pinhole of the same type positioned between the two pinholes of the type. For instance, two first pinholes are considered neighboring each other when there is no other first pinhole positioned in between such that the two first pinholes are right next to each other or spaced apart by one or more second pinholes. As another example, two second pinholes are considered neighboring each other when there is no other second pinhole positioned in between such that the two second pinholes are right next to each other or spaced apart by one or more first pinholes. Still taking the first pinhole 230, the first pinhole 240, the second pinhole 250, and the second pinhole 260 in FIG. 2A as an example, the second pinhole 250 may be positioned between the first pinholes 230 and 240. The first pinhole 240 may be positioned between the second pinholes 250 and 260. In some embodiments, a central angle between a first pinhole and a second pinhole that are adjacent to each other may be within an angel range, e.g., 1 degree~10 degrees, 2 degrees~8 degrees, 5 degrees~6 degrees, etc. As used herein, an angle between two pinholes is the angle between two lines each of which connects the central point of the collimator and one of the two pinholes. See, e.g., angle α in FIG. 2B.

Figure 8:
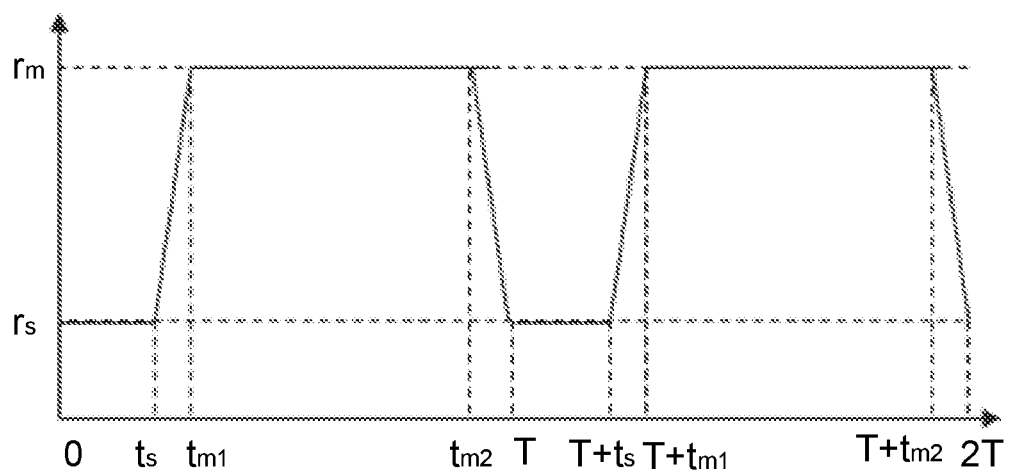
FIG. 8 is a schematic diagram illustrating an exemplary relationship between time and transmission ratio corresponding to a group of second pinholes according to some embodiments of the present disclosure.

In some embodiments, the group of second pinholes may be at the blocked configuration during a first time period (e.g., $0 \sim t_s$ in FIG. 8) and at the open configuration during a second time period (e.g., $t_{m_1} \sim t_{m_2}$ in FIG. 8). The second time period may be longer than the first time period. In some embodiments, a ratio of the second time period to the first time period may exceed a ratio threshold, e.g., 6, 5, 4, 3, etc.

In some embodiments, a first projection data set may be generated based on at least a portion of photons that traverse the collimator and are detected by the detector during the first time period when the plurality of second pinholes are at the blocked configuration. Accordingly, the first projection data set may include (substantially only) photons traversing the collimator through the group of first pinholes.

In some embodiments, a second projection data set may be generated based on at least a portion of photons that traverse the collimator and are detected by the detector during the second time period when the plurality of second pinholes are at the open configuration. Accordingly, the second projection data set may include a first portion that corresponds to photons traversing the collimator through the group of second pinholes at the open configuration and a second portion that corresponds to photons traversing the collimator through the group of first pinholes during the second time period.

In some embodiments, an image may be generated based on the first projection data set and the second projection data set. In some embodiments, the image may be generated using a reconstruction algorithm. For example, the reconstruction algorithm may include a maximum likelihood expectation maximization (MLEM) algorithm, an algebraic reconstruction technique (ART), a simultaneous algebraic reconstruction technique (SART), or the like, or any combination thereof.

In some embodiments, as described above, at least one of the first projection regions corresponding to the group of first pinholes may at least partially overlap at least one of the second projection regions corresponding to the group of second pinholes. Therefore, when the group of second pinholes are at the open configuration, a portion of the detector corresponding to each overlapping region may detect photons that traverse the collimator through at least one first pinhole corresponding to the overlapping region and photons that traverse the collimator through at least one second pinhole corresponding to the overlapping region. In such cases, the second projection data set that includes projection data corresponding to both photons traversing through the at least one first pinhole and photons traversing through the at least one second pinhole may be denoted as a multiplexing projection data set. If the image is generated directly using the first projection data set and the second projection data set, the image may have multiplexing artifacts caused by the multiplexing projection data set.

In order to reduce or avoid the multiplexing artifacts caused by the multiplexing projection data set, the first portion of the second projection data set and/or the second portion of the second projection data set may need to be separated. Since the photons may traverse the collimator (substantially only) through the group of first pinholes when the group of second pinholes are at the blocked configuration, the first projection data set may be considered to be generated based (substantially) solely on the photons that traverse the collimator through the group of first pinholes during the first time period. Therefore, the first portion of the second projection data set and/or the second portion of the second projection data set may be separated based on the first projection data set. In some embodiments, the separation of the first portion of the second projection data set and the second portion of the second projection data set may be performed based on an analytical approach. For instance, the second portion of the second projection data set may be (substantially) proportional to the first projection data set, depending on the length of the first time period compared to the length of the second time period. In some embodiments, the separation of the first portion of the second projection data set and the second portion of the second projection data set may be performed based on a statistical model (e.g., Formula (1) illustrated below). In some embodiments, the first portion of the second projection data set may be determined by subtracting the second portion of the second projection data set from the second projection data set. The image may be further generated based on at least one of the first projection data set, the first portion of the second projection data set, or the second portion of the second projection data set. In some embodiments, the image may be generated based on the first projection data set, the first portion of the second projection data set, and the second portion of the second projection data set. In some embodiments, the image may be generated based on the first projection data set and the first portion of the second projection data set.

In some embodiments, a switch from the blocked configuration to the open configuration of the group of second pinholes may take a third time period. In some embodiments, the third time period may be smaller than at least one of the first time period or the second time period. For example, the third timer period may be smaller than each of the first time period and the second time period. In some embodiments, the third time period may be smaller than a first time threshold (e.g., 1 second, 2 seconds).

In some embodiments, a third projection data set may be generated based on at least a portion of photons that traverse the collimator and are detected by the detector during the third time period. In some embodiments, the third projection data set may be used to generate the image together with the first projection data set and/or the second projection data set.

In some embodiments, a total duration of the first time period, the second time period, and the third time period may be set according to requirements of an image determined based on the projection data sets so acquired, for example, a quality of a reconstructed image, a reconstruction speed, etc. In some embodiments, a total duration of the first time period, the second time period, and the third time period may be smaller than a second time threshold (e.g., 30 seconds, 50 seconds, 60 seconds, 70 seconds), thereby achieving a real-time imaging (e.g., a real-time differential imaging). More descriptions of the image reconstruction may be found elsewhere in the present disclosure, for example, FIG. 7, FIG. 8, and the descriptions thereof.

FIG. 2A illustrates exemplary second pinholes at an open configuration according to some embodiments of the present disclosure. FIG. 2B illustrates exemplary second pinholes at a blocked configuration according to some embodiments of the present disclosure. The imaging device 200 may be an example of the imaging device 110.

In some embodiments, the imaging device 200 may include a collimator 210 and a detector 220. The collimator 210 may include a first pinhole 230, a first pinhole 240, a second pinhole 250, and a second pinhole 260 that are alternately positioned. In some embodiments, the first pinhole 230 and the first pinhole 240 may be at its open configuration in FIG. 2A and FIG. 2B. The second pinhole 250 and the second pinhole 260 may be at its open configuration in FIG. 2A and at its blocked configuration in FIG. 2B.

In some embodiments, the imaging device 200 may also include a filter 252 corresponding to the second pinhole 250 and a filter 262 corresponding to the second pinhole 260. As shown in FIG. 2A, the filter 252 may be positioned out of a photon pathway through the second pinhole 250, such that photons may traverse the collimator 210 through the second pinhole 250. The filter 262 may be positioned out of a photon pathway through the second pinhole 260 such that photons may traverse the collimator 210 through the second pinhole 260. The second pinhole 250, and the second pinhole 260 may be at the open configuration (e.g., a fully open configuration). Photons that impinge on the detector 220 may include a first portion traversing through the second pinholes 250 and 260 at the open configuration and a second portion traversing through the first pinholes 230 and 240.

As shown in FIG. 2A, a first projection region 234 corresponding to the first pinhole 230 and a first projection region 244 corresponding to the first pinhole 240 may overlap a second projection region 254 corresponding to the second pinhole 250. The second projection region 254 and a second projection region 264 corresponding to the second pinhole 260 may overlap the first projection region 244.

As shown in FIG. 2B, the filter 252 may be positioned to block the photon pathway through the second pinhole 250. The filter 262 may be positioned to block the photon pathway through the second pinhole 260. The second pinhole 250 and the second pinhole 260 may be at the blocked configuration. No photons traverse the collimator through the second pinholes 250 and 260 and photons that impinge on the detector 220 may traverse the collimator through the first pinhole 230 and 240.

In some embodiments, the filters 252 and 262 may be located on a ring 270. The ring 270 may be rotatable to adjust positions of the filters 252 and 262, such that the second pinholes 250 and 260 switch between the open configuration (e.g., in FIG. 2A) and the blocked configuration (e.g., in FIG. 2B). In some embodiments, the collimator 210 and the ring 270 may be arranged concentrically. It should be noted that FIG. 2A or FIG. 2B only illustrates a portion of the first pinholes, the second pinholes, and the filters, and the pinhole count of the first pinholes, the pinhole count of the second pinholes, or the count of the filters as illustrated are not intended to be limiting.

FIG. 3A and FIG. 3B are section views illustrating a portion of an exemplary imaging device according to some embodiments of the present disclosure. The imaging device 300 may be an example of the imaging device 110 or the imaging device 200.

As shown in FIG. 3A and FIG. 3B, the imaging device 300 may include a collimator 310 (e.g., a ring-shaped collimator) and a detector 320 (e.g., a ring-shaped detector). The collimator 310 may include a group of first pinholes 330 and a group of second pinholes 340. The first pinholes 330 and the second pinholes 340 may be at its open configuration. Photons that traverse the collimator 310 through each first pinhole 330 may correspond to a first projection region 334 defined by two adjacent solid lines 332. Photons that traverse the collimator 310 through each second pinhole 340 may correspond to a second projection region 344 defined by two adjacent dashed lines 342.

As shown in FIG. 3A and FIG. 3B, first projection regions 334 corresponding to the first pinholes 330 may be non-overlapping. The aggregate of the first projection regions 334 may cover the entire detector 320. Second projection regions 344 corresponding to the second pinholes 340 may be non-overlapping. The aggregate of the second projection regions 344 may cover the entire detector 320. The first projection region 334 and the second projection region 344 corresponding to the first pinhole 330 and the second pinhole 340 that are right next to each other may partially overlap. More descriptions of the imaging device 300 may be found elsewhere in the present disclosure, e.g., FIG. 1, 2A, 2B, or the descriptions thereof.

Figure 4:
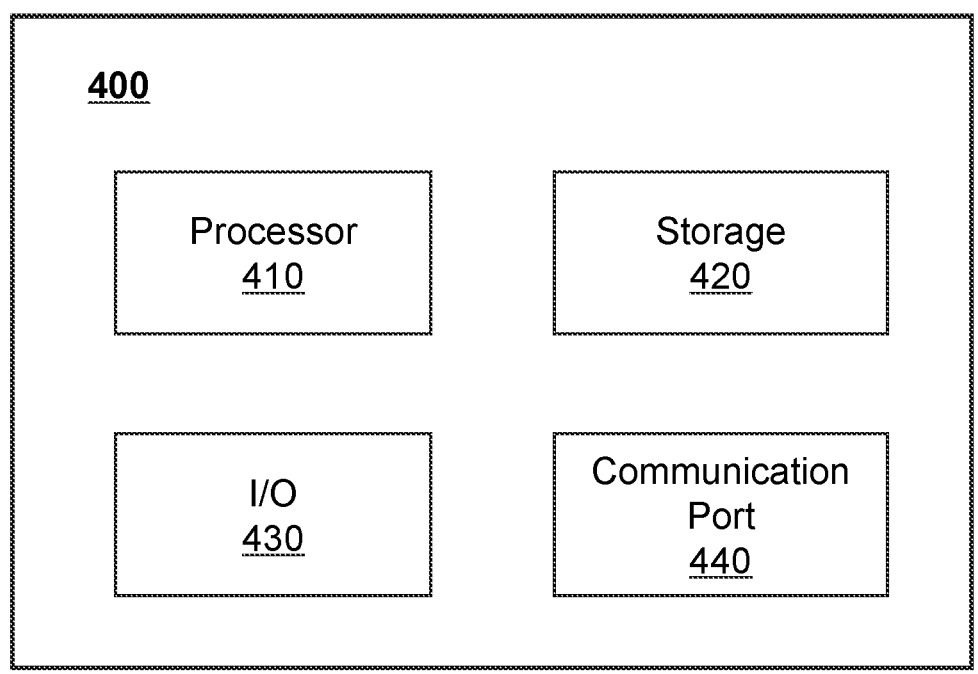
FIG. 4 is a schematic diagram illustrating hardware and/or software components of an exemplary computing device according to some embodiments of the present disclosure.

FIG. 4 is a schematic diagram illustrating exemplary hardware and/or software components of a computing device on which the processing device 120 may be implemented according to some embodiments of the present disclosure. As illustrated in FIG. 4, the computing device 400 may include a processor 410, a storage 420, an input/output (I/O) 430, and a communication port 440.

The processor 410 may execute computer instructions (program code) and perform functions of the processing device 120 in accordance with techniques described herein. The computer instructions may include routines, programs, objects, components, signals, data structures, procedures, modules, and functions, which perform particular functions described herein. For example, the processor 410 may process data obtained from the imaging device 110, the storage device 130, the terminal 140, or any other component of the imaging system 100. In some embodiments, the processor 410 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 400. However, it should be noted that the computing device 400 in the present disclosure may also include multiple processors, thus operations and/or method steps that are performed by one processor as described in the present disclosure may also be jointly or separately performed by the multiple processors. For example, if in the present disclosure the processor of the computing device 400 executes both step A and step B, it should be understood that step A and step B may also be performed by two different processors jointly or separately in the computing device 400 (e.g., a first processor executes step A and a second processor executes step B, or the first and second processors jointly execute steps A and B).

The storage 420 may store data/information obtained from the imaging device 110, the storage device 130, the terminal 140, or any other component of the imaging system 100. In some embodiments, the storage 420 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 420 may store one or more programs and/or instructions to perform exemplary methods described in the present disclosure.

The I/O 430 may input or output signals, data, or information. In some embodiments, the I/O 430 may enable a user interaction with the processing device 120. For example, the processing device 120 may display an image through the I/O 430. In some embodiments, the I/O 430 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)- based display, a flat panel display, a curved screen, a television device, a cathode ray tube (CRT), or the like, or a combination thereof.

The communication port 440 may be connected to a network (e.g., the network 150) to facilitate data communications. The communication port 440 may establish connections between the processing device 120 and the imaging device 110, the storage device 130, or the terminal 140. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 440 may be a standardized communication port, such as RS232, RS485, etc. In some embodiments, the communication port 440 may be a specially designed communication port. For example, the communication port 440 may be designed in accordance with the digital imaging and communications in medicine (DICOM) protocol.

Figure 5:
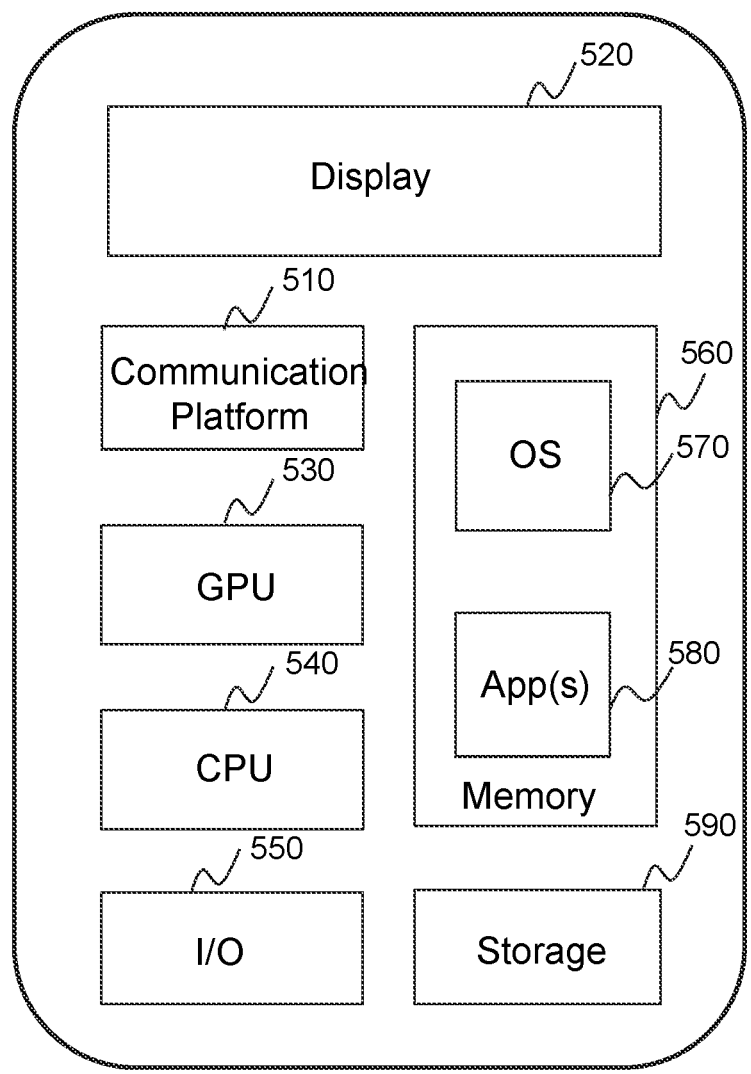
FIG. 5 is a schematic diagram illustrating hardware and/or software components of an exemplary mobile device according to some embodiments of the present disclosure.

FIG. 5 is a schematic diagram illustrating exemplary hardware and/or software components of a mobile device on which the terminal 140 may be implemented according to some embodiments of the present disclosure. As illustrated in FIG. 5, the mobile device 500 may include a communication platform 510, a display 520, a graphics processing unit (GPU) 530, a central processing unit (CPU) 540, an I/O 550, a memory 560, and a storage 590. In some embodiments, any other suitable component, including a system bus or a controller (not shown), may also be included in the mobile device 500. In some embodiments, a mobile operating system 570 (e.g., iOS, Android, Windows Phone, etc.) and one or more applications 580 may be loaded into the memory 560 from the storage 590 in order to be executed by the CPU 540. The applications 580 may include a browser or any other suitable mobile apps for receiving and rendering information relating to imaging or other information from the processing device 120. User interactions with the information stream may be achieved via the I/O 550 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the radiation therapy as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 6:
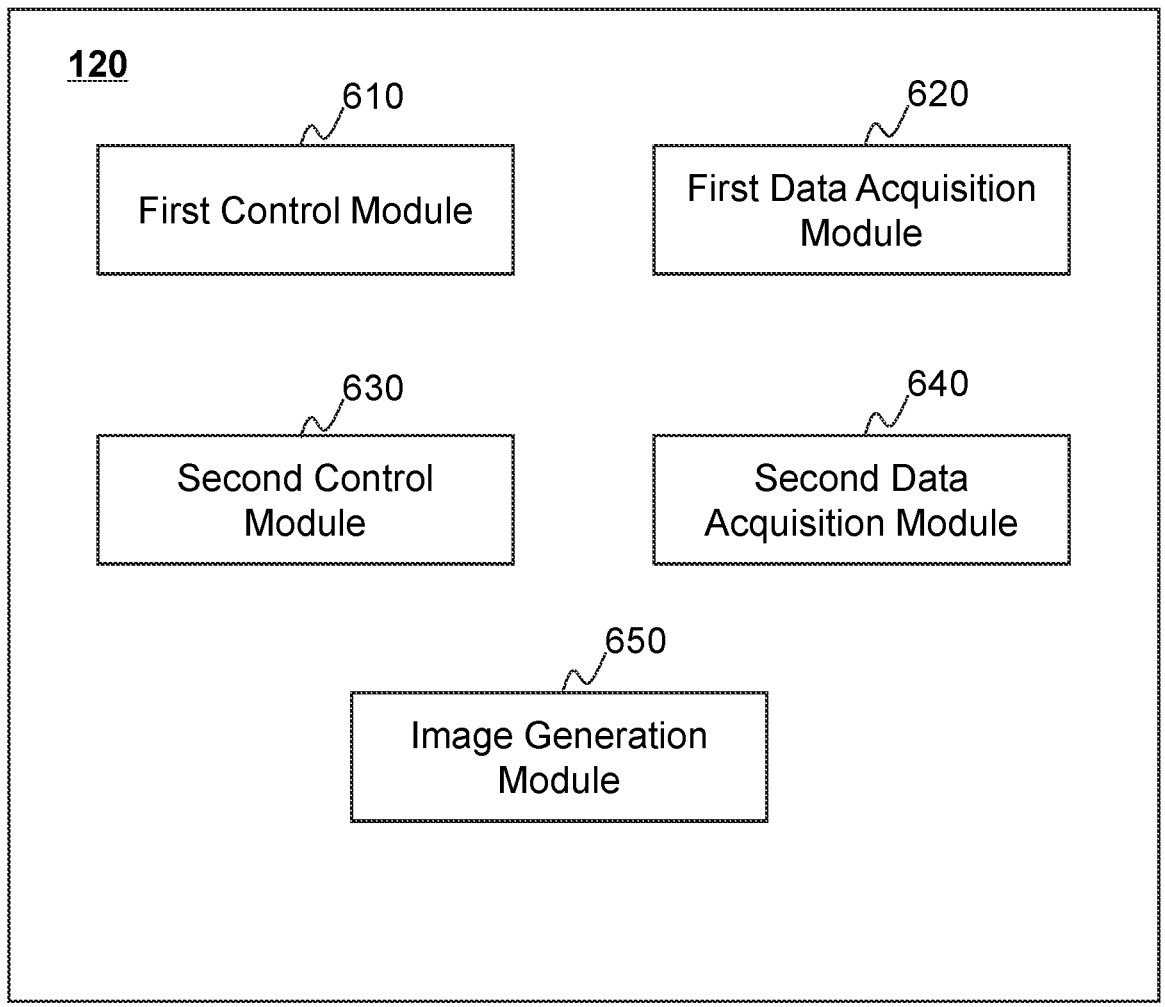
FIG. 6 is a block diagram illustrating an exemplary processing device according to some embodiments of the present disclosure.

FIG. 6 is a block diagram illustrating an exemplary processing device according to some embodiments of the present disclosure. The processing device 120 may include a first control module 610, a first data acquisition module 620, a second control module 630, a second data acquisition module 640, and an image generation module 650.

In some embodiments, an imaging device (e.g., a SPECT device) of an imaging system may include a collimator and a detector. The collimator may include a group of first pinholes and a group of second pinholes. The group of first pinholes may be configured to remain open. The group of second pinholes may be configured to alternate between an open configuration and a blocked configuration. The collimator may be configured to allow photons to traverse the collimator through at least one group of the group of first pinholes or the group of second pinholes. The detector may be configured to detect at least a portion of the photons that have traversed the collimator. The imaging device may be similar to the imaging device described in FIG. 1-3B, the descriptions of which are not repeated here.

The first control module 610 may be configured to cause the group of second pinholes to maintain at the blocked configuration during a first time period. In some embodiments, the imaging device may include a plurality of filters. The first control module 610 may cause the plurality of filters to move to a position (e.g., the second position described in FIG. 1) such that the group of second pinholes are at the blocked configuration.

The first data acquisition module 620 may be configured to acquire a first projection data set during the first time period. In some embodiments, the first data acquisition module 620 may generate the first projection data set based on at least a portion of photons that traverse the collimator and are detected by the detector during the first time period.

The second control module 630 may be configured to cause the group of second pinholes to maintain at the open configuration during a second time period. In some embodiments, the second control module 630 may cause the plurality of filters to move at a position (e.g., the first position described in FIG. 1) to unblock the group of second pinholes so that the group of second pinholes may be at the open configuration.

The second data acquisition module 640 may be configured to acquire a second projection data set during the second time period. In some embodiments, the second data acquisition module 640 may generate the second projection data set based on at least a portion of photons that traverse the collimator and are detected by the detector during the second time period.

The image generation module 650 may be configured to generate an image based on the first projection data set and the second projection data set. In some embodiments, the second projection data set may include a first portion that corresponds to photons traversing the collimator through the group of second pinholes at the open configuration and a second portion that corresponds photons traversing the collimator through the group of first pinholes. The image generation module 650 may separate the first portion of the second projection data set and the second portion of the second projection data set based on the first projection data set. The image generation module 650 may generate the image based on at least one of the first projection data set, the first portion of the second projection data set, or the second portion of the second projection data set. More descriptions of the modules may be found elsewhere in the present disclosure, for example, FIG. 7 or the descriptions thereof.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module. The storage module may be configured to store data generated during any process performed by any component of the processing device 120. As another example, each of the components of the processing device 120 may include a storage apparatus. Additionally or alternatively, the components of the processing device 120 may share a common storage apparatus.

Figure 7:
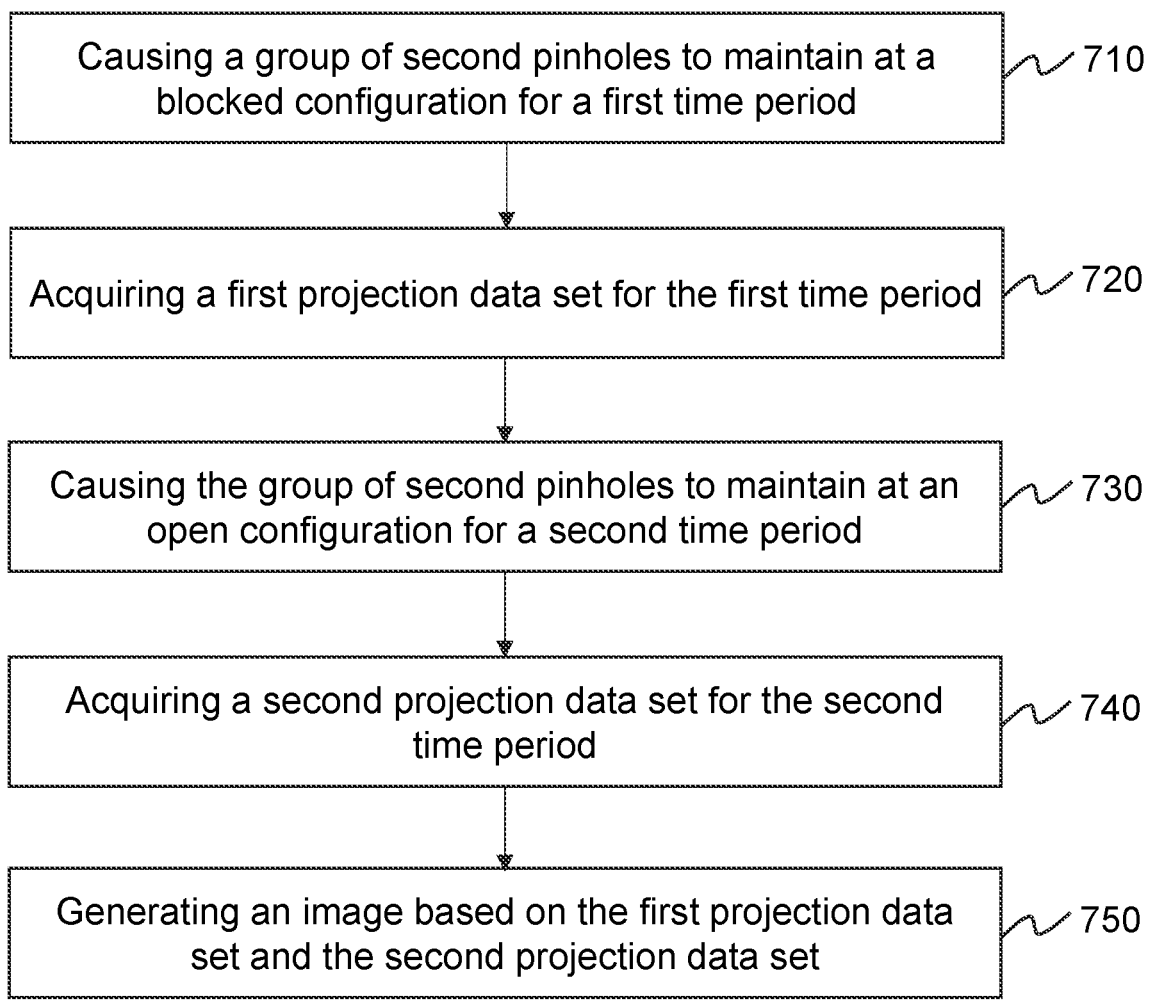
FIG. 7 is a flowchart illustrating an exemplary imaging process of an imaging system according to some embodiments of the present disclosure.

FIG. 7 is a flowchart illustrating an exemplary imaging process of an imaging system according to some embodiments of the present disclosure. The process 700 may be implemented in the imaging system 100 illustrated in FIG. 1. For example, the process 700 may be stored in the storage device 130 and/or the storage 420 in the form of instructions (e.g., an application), and invoked and/or executed by the processing device 120 (e.g., the processor 410 illustrated in FIG. 4, or one or more modules in the processing device 120 illustrated in FIG. 6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In some embodiments, an imaging device (e.g., a SPECT device) of the imaging system may include a collimator and a detector. The collimator may include a group of first pinholes and a group of second pinholes. The group of first pinholes may be configured to remain open. The group of second pinholes may be configured to alternate between an open configuration and a blocked configuration. The collimator may be configured to allow photons to traverse the collimator through at least one group of the group of first pinholes or the group of second pinholes. The detector may be configured to detect at least a portion of the photons that have traversed the collimator. The imaging device may be similar to the imaging device described in FIG. 1-3B, the descriptions of which are not repeated here.

In 710, the processing device 120 (e.g., the first control module 610) may cause the group of second pinholes to maintain at the blocked configuration during a first time period. As described in FIGS. 1-2B, when the group of second pinholes are at the blocked configuration, photons may mainly traverse the collimator through the group of first pinholes and (substantially) no photons traverse the collimator through the group of second pinholes. Accordingly, a transmission ratio (also referred to as the first transmission ratio as illustrated above) corresponding to the group of second pinholes at the blocked configuration may be smaller than a first ratio threshold (e.g., 0.0001, 0.001, 0.01). In some embodiments, when the group of second pinholes are at the blocked configuration, no photons traverse the collimator through the group of second pinholes, and photons may only traverse the collimator through the group of first pinholes.

In some embodiments, the imaging device may include a plurality of filters. The processing device 120 may cause the plurality of filters to move to a position (e.g., the second position described in FIG. 1) such that the group of second pinholes are at the blocked configuration.

In 720, the processing device 120 (e.g., the first data acquisition module 620) may acquire a first projection data set during the first time period. In some embodiments, the first projection data set may be generated based on at least a portion of photons that traverse the collimator and are detected by the detector during the first time period.

In 730, the processing device 120 (e.g., the second control module 630) may cause the group of second pinholes to maintain at the open configuration during a second time period. In some embodiments, the processing device 120 may cause the plurality of filters to move at a position (e.g., the first position described in FIG. 1) to unblock the group of second pinholes so that the group of second pinholes may be at the open configuration. A transmission ratio (also referred to as the second transmission ratio as illustrated above) corresponding to the group of second pinholes at the open configuration may exceed a second ratio threshold (e.g., 0.9999, 0.999, 0.99).

In some embodiments, when the group of second pinholes are at the open configuration, photons traversing through the collimator may include a first portion that traverses the collimator through the group of second pinholes and a second portion that traverses the collimator through the group of first pinholes. In some embodiments, the second time period may be longer than the first time period. A ratio of the second time period to the first time period may exceed a ratio threshold, e.g., 6, 5, 4, 3, etc.

In 740, the processing device 120 (e.g., the second data acquisition module 640) may acquire a second projection data set during the second time period. In some embodiments, the second projection data set may be generated based on at least a portion of photons that traverse the collimator and are detected by the detector during the second time period. As described in operation 730, the photons may traverse the collimator both through the group of first pinholes and the group of second pinholes during the second time period. Accordingly, the second projection data set may include a first portion that corresponds to photons traversing the collimator through the group of second pinholes at the open configuration and a second portion that corresponds to photons traversing the collimator through the group of first pinholes during the second time period.

In 750, the processing device 120 (e.g., the image generation module 650) may generate an image based on the first projection data set and the first portion of the second projection data set. In some embodiments, the processing device 120 may generate the image using a reconstruction algorithm. For example, the reconstruction algorithm may include a maximum likelihood expectation maximization (MLEM) algorithm, an algebraic reconstruction technique (ART), a simultaneous algebraic reconstruction technique (SART), or the like, or any combination thereof.

In some embodiments, as described in FIGS. 1-3B, photons that traverse the collimator through each first pinhole of the group of first pinholes may correspond to a first projection region, and the first projection regions corresponding to the group of first pinholes may be non-overlapping. Photons that traverse the collimator through each second pinhole of the group of second pinholes may correspond to a second projection region, and the second projection regions corresponding to the group of second pinholes may be non-overlapping. At least one of the first projection regions may at least partially overlap at least one of the second projection regions. Therefore, when the group of second pinholes are at the open configuration, a portion of the detector corresponding to each overlapping region may detect photons that traverse the collimator through at least one first pinhole corresponding to the overlapping region and photons that traverse the collimator through at least one second pinhole corresponding to the overlapping region. In such cases, the second projection data set that includes projection data corresponding to both photons traversing through the at least one first pinhole and photons traversing through the at least one second pinhole may be denoted as a multiplexing projection data set. If the image is generated directly using the first projection data set and the second projection data set, the image may have multiplexing artifacts caused by the multiplexing projection data set.

In order to reduce or avoid the multiplexing artifacts caused by the multiplexing projection data set, the first portion of the second projection data set and/or the second portion of the second projection data set may need to be separated. Since the photons may traverse the collimator (substantially only) through the group of first pinholes when the group of second pinholes are at the blocked configuration, the first projection data set may be considered to be generated based (substantially) solely on the photons that traverse the collimator through the group of first pinholes during the first time period. Therefore, the processing device 120 may separate the first portion of the second projection data set and/or the second portion of the second projection data set based on the first projection data set. For instance, the second portion of the second projection data set may be (substantially) proportional to the first projection data set, depending on the length of the first time period compared to the length of the second time period. In some embodiments, the processing device 120 may determine the first portion of the second projection data set by subtracting the second portion of the second projection data set from the second projection data set.

Further, the processing device 120 may determine the image based on at least one of the first projection data set, the first portion of the second projection data set, or the second portion of the second projection data set. In some embodiments, the processing device 120 may generate the image based on the first projection data set, the first portion, and the second portion. In some embodiments, the processing device 120 may generate the image based on the first projection data set and the first portion of the second projection data set.

In some embodiments, the processing device 120 may generate the image according to Formula (1) below:

$$\begin{bmatrix} y_s \\ y_m \end{bmatrix} = \begin{bmatrix} A_1 + r_s A_2 \\ A_1 + r_m A_2 \end{bmatrix} x \quad (1)$$

where x refers to the image, $r_s$ refers to the first transmission ratio, $r_m$ refers to the second transmission ratio, $y_s$ refers to the first projection data set, $y_m$ refers to the second projection data set, $A_1$ refers to a first matrix (e.g., a projection matrix) of the group of first pinholes, and $A_2$ refers to a second matrix (e.g., a projection matrix) of the group of second pinholes. As used herein, the first matrix may be used to faciliate a forward projection operation on the image through the group of first pinholes. The second matrix may be used to faciliate a forward projection operation on the image through the group of second pinholes. An element of the first matrix or an element of the second matrix may represent a probability that a photon emitted from a pixel of the image reaches a point of the detector. In some embodiments, an element of the first matrix or an element of the second matrix may include a projection coefficient. The projection coefficient may represent average photons detected by a detector unit of the detector for per unit of radioactivity generated by a pixel of the image when the group of first pinholes and the group of second pinholes are both at the open configuration. In some embodiments, the projection coefficient may relate to a configuration of the imaging system, the sensitivity of the detector, or the like, or a combination thereof.

In some embodiments, a switch from the blocked configuration to the open configuration of the group of second pinholes may take a third time period. In some embodiments, the third time period may be smaller than at least one of the first time period or the second time period. For example, the third timer period may be smaller than each of the first time period and the second time period. In some embodiments, the third time period may be smaller than a first time threshold (e.g., 1 second, 2 seconds).

In some embodiments, the processing device 120 may acquire a third projection data set based on at least a portion of photons that traverse the collimator and are detected by the detector during the third time period. In some embodiments, the third projection data set may be used to generate the image together with the first projection data set and the second projection data set.

In some embodiments, a total duration of the first time period, the second time period, and the third time period may be set according to requirements of an image determined based on the projection data sets so acquired, for example, a quality of a reconstructed image, a reconstruction speed, etc. In some embodiments, a total duration of the first time period, the second time period, and the third time period may be smaller than a second time threshold (e.g., 30 seconds, 50 seconds, 60 seconds, 70 seconds), thereby achieving a real-time imaging.

FIG. 8 is a schematic diagram illustrating an exemplary relationship between time and transmission ratio corresponding to a group of second pinholes according to some embodiments of the present disclosure.

In some embodiments, an imaging device (e.g., a SPECT device) of the imaging system may include a collimator and a detector. The collimator may include a group of first pinholes and a group of second pinholes. The group of first pinholes may be configured to remain open. The group of second pinholes may be configured to alternate between an open configuration and a blocked configuration. The collimator may be configured to allow photons to traverse the collimator through at least one group of the group of first pinholes or the group of second pinholes. The detector may be configured to detect at least a portion of the photons that have traversed the collimator. The imaging device may be similar to the imaging device described in FIGS. 1-3B and FIG. 7, the descriptions of which are not repeated here.

In some embodiments, the group of second pinholes may be at the blocked configuration during a first time period, e.g., $0 \sim t_s$ in FIG. 8. A transmission ratio corresponding to the group of second pinholes at the blocked configuration may be denoted as $r_s$ in FIG. 8. $r_s$ may be smaller than a first ratio threshold (e.g., 0.00001, 0.0001, 0.001). The group of second pinholes may be at the open configuration during a second time period, e.g., $t_{m_1} \sim t_{m_2}$ in FIG. 8. A transmission ratio corresponding to the group of second pinholes at the open configuration may be denoted as $r_m$ in FIG. 8. $r_m$ may exceed a second ratio threshold (e.g., 0.9999, 0.999, 0.99). For example, $r_m$ may be equal to 1. The group of second pinholes may be switched from the blocked configuration to the open configuration during a third time period, e.g., $t_s \sim t_m$ in FIG. 8. The group of second pinholes may be switched from the open configuration to the blocked configuration during a fourth time period, e.g., $t_{m2} \sim t_T$ in FIG. 8. The fourth time period may be equal to the third time period.

As shown in FIG. 8, the first time period may be larger than the third (or fourth) time period. The second time period may be larger than the third (or fourth) time period. The second time period may be larger than the first time period. A total duration of the first time period, the second time period, the third time period, and the fourth time period may be denoted as T in FIG. 8. In some embodiments, T may be set according to requirements of an image determined based on projection data sets acquired during time periods (e.g., the first time period, the second time period, the third time period, the fourth time period), respectively, for example, a quality of a reconstructed image, a reconstruction speed, etc. In some embodiments, T may be smaller than a time threshold (e.g., 30 seconds, 50 seconds, 60 seconds, 70 seconds), thereby achieving a real-time imaging.

In some embodiments, a first image may be generated based on a first projection data set acquired during the first time period and a second projection data set during the second time period. In some embodiments, by repeatedly setting the configuration of the group of second pinholes as illustrated above, a second image may be generated based on a projection data set acquired during a time period (T~T+$t_s$) as illustrated in FIG. 8 and a projection data set acquired during a time period ((T+$t_{m1}$)~(T+$t_{m2}$)) as illustrated in FIG. 8. In some embodiments, the generation of the first image or the second image may be the same as or similar to the process for generating the image as illustrated in FIG. 2 or FIG. 7, the descriptions of which are not repeated herein.

It should be noted that the above descriptions are for illustration purposes. In some embodiments, the detector may include more than two groups of pinholes. One group of the more than two groups of pinholes may be configured to remain open similar to the group of first pinholes, and each of other groups of pinholes may be configured to alternate between the open configuration and the blocked configuration similar to the group of second pinholes. In some embodiments, first time periods corresponding to the other groups of pinholes may be different. Second time periods corresponding to the other groups of pinholes may be different. In some embodiments, transmission ratios corresponding to the other groups of pinholes may be different. In some embodiments, second projection regions corresponding to the other groups of pinholes may be different.

In some embodiments of the present disclosure, the imaging device 110 of the imaging system 100 may include a collimator and a detector. The collimator may include a group of first pinholes and a group of second pinholes. The collimator may be configured to allow photons to traverse the collimator through at least one group of the group of first pinholes or the group of second pinholes. The detector may be configured to detect at least a portion of the photons that have traversed the collimator.

In some embodiments, the group of first pinholes may be configured to alternate between an open configuration and a blocked configuration. The group of second pinholes may be configured to alternate between an open configuration and a blocked configuration. The group of first pinholes and the group of second pinholes may be configured to implement any one of a plurality of pinhole modes including a first pinhole mode, a second pinhole mode, and a third pinhole mode. In the first pinhole mode, the group of first pinholes may be configured at the blocked configuration, while the group of second pinholes may be configured at the open configuration. In the second pinhole mode, the group of first pinholes and the group of second pinholes may both be configured at the open configuration. In the third pinhole mode, the group of first pinholes may be configured at the open configuration, while the group of second pinholes may be configured at the blocked configuration.

In some embodiments, the group of first pinholes may be configured to allow a first portion of the photons to traverse at the open configuration and a second portion of the photons to traverse at the blocked configuration. In some embodiments, a ratio (also referred to as "a first transmission ratio") of the second portion to the first portion may be smaller than a first ratio threshold (e.g., 0.0001, 0.001, 0.01), that is, (substantially) no photons traverse the collimator through the group of first pinholes at the blocked configuration. In some embodiments, the ratio of the second portion to the first portion may be zero, that is, no photons traverse the collimator through the group of first pinholes at the blocked configuration.

In some embodiments, in the open configuration of a first pinhole, the first pinhole may be fully open to allow photons to pass through or partially open and partially blocked such that only a portion of the first pinhole is available for photons to pass through. In some embodiments, a transmission ratio (also referred to as a second transmission ratio) corresponding to the group of first pinholes at the open configuration may exceed a second ratio threshold (e.g., 0.9999, 0.999, 0.99).

In some embodiments, the group of second pinholes may be configured to allow a first portion of the photons to traverse at the open configuration and a second portion of the photons to traverse at the blocked configuration. In some embodiments, a ratio (also referred to as "a third transmission ratio") of the second portion to the first portion may be smaller than a third ratio threshold (e.g., 0.0001, 0.001, 0.01); that is, (substantially) no photons traverse the collimator through the group of second pinholes at the blocked configuration. For instance, the ratio of the second portion to the first portion may be zero; that is, no photons traverse the collimator through the group of second pinholes at the blocked configuration. In some embodiments, the first transmission ratio may be the same as the third transmission ratio. In some embodiments, the first transmission ratio may be different from the third transmission ratio.

In some embodiments, in the open configuration of a second pinhole, the second pinhole may be fully open to allow photons to pass through or partially open and partially blocked such that only a portion of the second pinhole is available for photons to pass through. In some embodiments, a transmission ratio (also referred to as a fourth transmission ratio) corresponding to the group of second pinholes at the open configuration may exceed a fourth ratio threshold (e.g., 0.9999, 0.999, 0.99). In some embodiments, the second transmission ratio may be the same as the fourth transmission ratio. In some embodiments, the second transmission ratio may be different from the fourth transmission ratio.

In some embodiments, the imaging device 110 may include a plurality of filters. The plurality of filters may be configured to facilitate the group of first pinholes to switch between the open configuration and the blocked configuration and the group of second pinholes to switch between the open configuration and the blocked configuration such that various pinhole modes including, e.g., the first pinhole mode, the second pinhole mode, and the third pinhole mode, may be implemented.

Figure 9A:
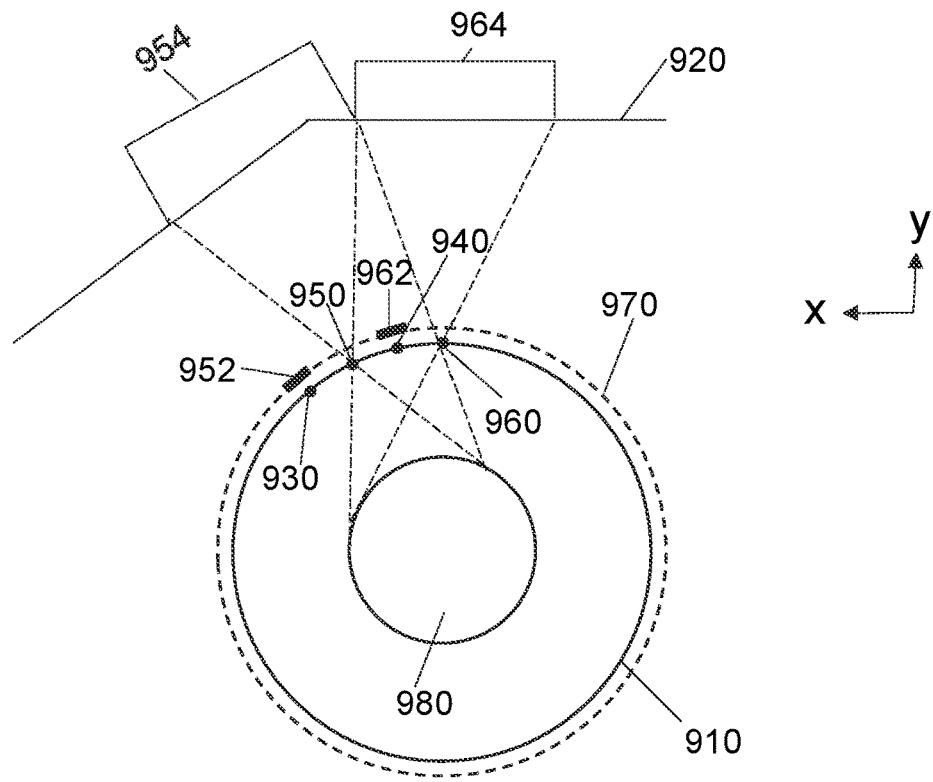
FIG. 9A illustrates an exemplary first pinhole mode in which first pinholes are at a blocked configuration and second pinholes are at an open configuration according to some embodiments of the present disclosure.
Figure 9B:
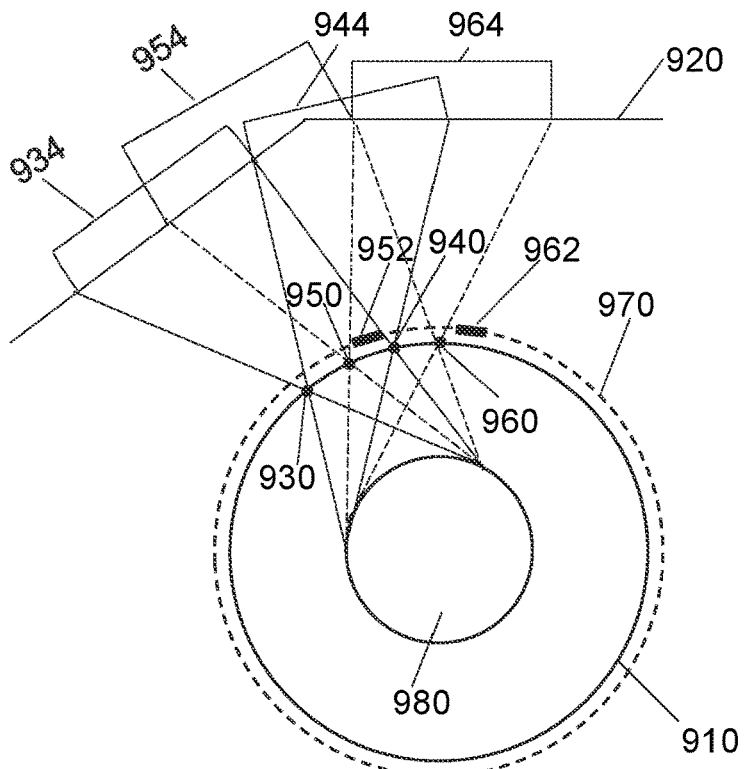
FIG. 9B illustrates an exemplary second pinhole mode in which first pinholes are at an open configuration and second pinholes are at an open configuration according to some embodiments of the present disclosure.
Figure 9C:
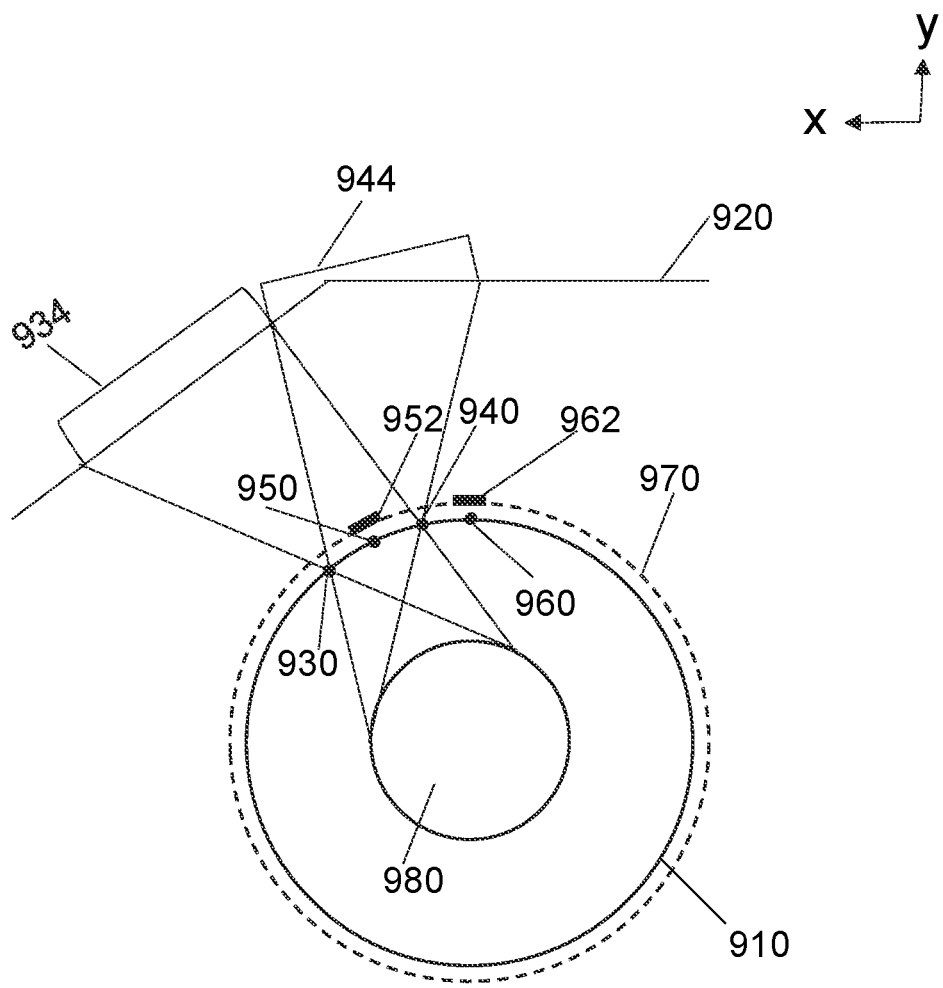
FIG. 9C illustrates an exemplary third pinhole mode in which first pinholes are at an open configuration and second pinholes are at blocked configuration according to some embodiments of the present disclosure.

In some embodiments, each of the plurality of filters may correspond to at least one first pinhole of the group of first pinholes or at least one second pinhole of the group of second pinholes such that the movement of the filter may facilitate the corresponding at least one first pinhole and the corresponding at least one second pinhole to switch between the open configuration and the blocked configuration. For example, each of the plurality of filters may correspond to one first pinhole of the group of first pinholes and one second pinhole of the group of second pinholes (e.g., as illustrated in FIGS. 9A-9C) such that the movement of the filter may facilitate the corresponding first pinhole and the corresponding second pinhole to switch between the open configuration and the blocked configuration. As another example, each of the plurality of filters may correspond to two or more first pinholes of the group of first pinholes and two or more second pinholes of the group of second pinholes such that the movement of the filter may facilitate each of the corresponding two or more first pinholes and each of the corresponding two or more second pinholes to switch between the open configuration and the blocked configuration.

In some embodiments, each of the plurality of filters may be movable between a first position, a second position, and a third position. When a filter is at its first position (e.g., as illustrated in FIG. 9A), the filter may (substantially) block a photon pathway through at least one first pinhole corresponding to the filter. The at least one corresponding first pinhole may be at the blocked configuration. When the filter is at the first position, the filter may be positioned out of a photon pathway through at least one second pinhole corresponding to the filter. The at least one corresponding second pinhole may be at the open configuration.

In some embodiments, when a filter is at the second position (e.g., as illustrated in FIG. 9B), the filter may be positioned out of a photon pathway through at least one first pinhole corresponding to the filter. The at least one corresponding first pinhole may be at the open configuration. When the filter is at the second position, the filter may be positioned out of a photon pathway through at least one second pinhole corresponding to the filter. The at least one corresponding second pinhole may be at the open configuration.

In some embodiments, when a filter is at the third position (e.g., as illustrated in FIG. 9C), the filter may be positioned out of a photon pathway through at least one first pinhole corresponding to the filter. The at least one corresponding first pinhole may be at the open configuration. When the filter is at the third position, the filter may (substantially) block a photon pathway through at least one second pinhole corresponding to the filter. The at least one corresponding second pinhole may be at the blocked configuration.

In some embodiments, when the filters are at their respective first positions, the group of first pinholes and the group of second pinholes may be at the first pinhole mode. When the filters are at their respective second positions, the group of first pinholes and the group of second pinholes may be at the second pinhole mode. When the filter is at their respective third positions, the group of first pinholes and the group of second pinholes may be at the third pinhole mode.

FIG. 9A illustrates an exemplary first pinhole mode in which the first pinholes are at a blocked configuration and the second pinholes are at an open configuration according to some embodiments of the present disclosure. FIG. 9B illustrates an exemplary second pinhole mode in which the first pinholes are at an open configuration and the second pinholes are at an open configuration according to some embodiments of the present disclosure. FIG. 9C illustrates an exemplary third pinhole mode in which the first pinholes are at an open configuration and the second pinholes are at blocked configuration according to some embodiments of the present disclosure. The imaging device 900 may be an example of the imaging device 110.

In some embodiments, the imaging device 900 may include a collimator 910 and a detector 920. The collimator 910 may include a group of first pinholes including first pinholes 930 and 940, and a group of second pinholes including second pinholes 950 and 960. The first pinholes and the second pinholes may be alternately positioned. In some embodiments, the first pinhole 930 and the first pinhole 940 may be at its blocked configuration as illustrated in FIG. 9A and at its open configuration as illustrated in FIG. 9B and FIG. 9C. The second pinhole 950 and the second pinhole 960 may be at its open configuration as illustrated in FIG. 9A and FIG. 9B and at its blocked configuration as illustrated in FIG. 9C.

In some embodiments, the imaging device 900 may also include a filter 952 corresponding to the first pinhole 930 and the second pinhole 950 and a filter 962 corresponding to the first pinhole 940 and the second pinhole 960. In the exemplary first pinhole mode as shown in FIG. 9A, the filter 952 may be positioned out of a photon pathway through the second pinhole 950 and block a photon pathway through the first pinhole 930, such that photons may traverse the collimator 910 through the second pinhole 950. The filter 962 may be positioned out of a photon pathway through the second pinhole 960 and block a photon pathway through the first pinhole 940 such that photons may traverse the collimator 910 through the second pinhole 960. No photons traverse the collimator through the first pinholes 930 and 940, and photons that impinge on the detector 920 may traverse the collimator through the second pinholes 950 and 960.

In the exemplary second pinhole mode as shown in FIG. 9B, the first pinhole 930, the first pinhole 940, the second pinhole 950, and the second pinhole 960 may be at the open configuration (e.g., a fully open configuration). Photons that impinge on the detector 920 may include a first portion traversing through the second pinholes 950 and 960 at the open configuration and a second portion traversing through the first pinholes 930 and 940 at the open configuration.

In the exemplary third pinhole mode as shown in FIG. 9C, the filter 952 may be positioned out of a photon pathway through the first pinhole 930 and block a photon pathway through the second pinhole 950, such that photons may traverse the collimator 910 through the first pinhole 930. The filter 962 may be positioned out of a photon pathway through the first pinhole 940 and block a photon pathway through the second pinhole 960 such that photons may traverse the collimator 910 through the first pinhole 940. No photons traverse the collimator through the second pinholes 950 and 960 and photons that impinge on the detector 920 may traverse the collimator 910 through the first pinhole 930 and 940.

In some embodiments, photons that traverse the collimator 910 through the first pinhole 930 at the open configuration may correspond to a first projection region 934. In some embodiments, photons that traverse the collimator through the first pinhole 940 at the open configuration may correspond to a first projection region 944. In some embodiments, photons that traverse the collimator through the second pinhole 950 at the open configuration may correspond to a second projection region 954. In some embodiments, photons that traverse the collimator through the second pinhole 960 at the open configuration may correspond to a second projection region 964. As shown in FIG. 9B, the first projection region 934 corresponding to the first pinhole 930 and the first projection region 944 corresponding to the first pinhole 940 may overlap the second projection region 954 corresponding to the second pinhole 950. The second projection region 954 and the second projection region 964 corresponding to the second pinhole 960 may overlap the first projection region 944.

In some embodiments, the filters 952 and 962 may be located on a ring 970. The ring 970 may be rotatable to adjust positions of the filters 952 and 962, such that the first pinholes 930 and 940 and the second pinholes 950 and 960 may switch between the open configuration and the blocked configuration, respectively. In some embodiments, the collimator 910 and the ring 970 may be arranged concentrically. It should be noted that FIG. 9A or FIG. 9B only illustrates a portion of the first pinholes, the second pinholes, and the filters, and the pinhole count of the first pinholes, the pinhole count of the second pinholes, or the count of the filters as illustrated are not intended to be limiting.

Figure 10:
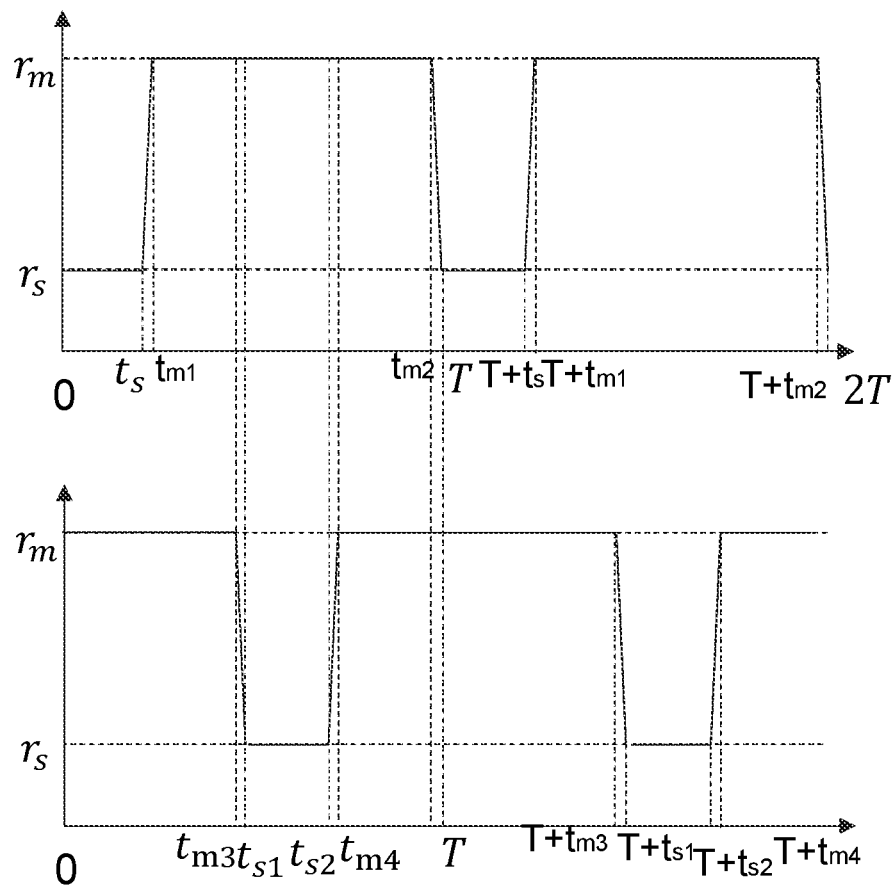
FIG. 10 is a schematic diagram illustrating an exemplary relationship between time and transmission ratio corresponding to a group of first pinholes and a group of second pinholes according to some embodiments of the present disclosure.

FIG. 10 is a schematic diagram illustrating an exemplary relationship between time and transmission ratio corresponding to the group of first pinholes and the group of second pinholes according to some embodiments of the present disclosure.

In some embodiments, the group of first pinholes may be at the blocked configuration during a first time period (e.g., $0 \sim t_s$ in FIG. 10) and at the open configuration during a second time period (e.g., $t_{m_1} \sim t_{m_2}$ in FIG. 10). The second time period may be different from the first time period. For instance, the second time period may be longer than the first time period. In some embodiments, a ratio of the second time period to the first time period may exceed a ratio threshold, e.g., 6, 5, 4, 3, etc.

In some embodiments, the group of second pinholes may be at the blocked configuration during a third time period (e.g., $t_{s_1} \sim t_{s_2}$ in FIG. 10) and at the open configuration during a fourth time period (e.g., $0 \sim t_{m_3}$ and $t_{m_4} \sim T$ in FIG. 10). The fourth time period may be different from the third time period. For instance, the fourth time period may be longer than the third time period. In some embodiments, a ratio of the fourth time period to the third time period may exceed a ratio threshold, e.g., 6, 5, 4, 3, etc.

In some embodiments, the first time period may be different from the third time period. In some embodiments, the first time period may be (substantially) equal to the third time period. In some embodiments, the second time period may partially overlap the fourth time period. In some embodiments, the second time period may (substantially) coincide with the fourth time period. In some embodiments, the first transmission ratio may be the same as the third transmission ratio denoted as $r_s$ in FIG. 10. The second transmission ratio may be the same as the fourth transmission ratio denoted as $r_m$ in FIG. 10.

In some embodiments, the first pinhole mode may be implemented during the first time period in which the group of first pinholes may be configured at the blocked configuration and the group of second pinholes may be configured at the open configuration. The third pinhole mode may be implemented during the third time period in which the group of first pinholes may be configured at the open configuration and the group of second pinholes may be configured at the blocked configuration. The third pinhole mode may be implemented during a fifth third time period (e.g., $t_{m_1} \sim t_{m_3}$ and $t_{m_4} \sim t_{m_2}$ in FIG. 10 in which group of first pinholes and the group of second pinholes may be configured at the open configuration. The fifth time period may be different from the first time period and the third time period, respectively.

In some embodiments, a switch from the blocked configuration to the open configuration of the group of first pinholes or the group of second pinholes may occur during a sixth time period (e.g., $t_s \sim t_{m_1}$ or $t_{s_2} \sim t_{m_4}$ in FIG. 10). A switch from the open configuration to the blocked configuration of the group of first pinholes or the group of second pinholes may occur during a seventh time period (e.g., $t_{m_2} \sim T$ or $t_{m_3} \sim t_{s_1}$ in FIG. 10). In some embodiments, the sixth time period may be (substantially) equal to the seventh time period. The sixth time period or the seventh time period may be shorter than at least one of the first time period, the second time period, the third time period, the fourth time period, or the fifth time period.

In some embodiments, the fifth time period may be a portion of the second time period. For example, the second time period may include the third time period and the fifth time period, as well as the sixth time period and the seventh time period during which a switch between the blocked configuration and the open configuration of the group of second pinholes occurs. In some embodiments, the fifth time period may be a portion of the fourth time period. For example, the fourth time period may include the first time period and the fifth time period, as well as the sixth time period and the seventh time period during which a switch between the blocked configuration and the open configuration of the group of first pinholes occurs.

A total duration of the first time period, the second time period, the sixth time period, and the seventh time period may be denoted as T in FIG. 10. A total duration of the third time period, the fourth time period, the sixth time period, and the seventh time period may be denoted as T in FIG. 10. In some embodiments, T may be set according to requirements of an image determined based on projection data sets acquired during time periods (e.g., the first time period, the second time period, the third time period, the fourth time period), respectively, for example, a quality of a reconstructed image, a reconstruction speed, etc.

In some embodiments, a first projection data set may be generated based on at least a portion of photons that traverse the collimator and are detected by the detector during the first time period when the plurality of first pinholes are at the blocked configuration and the plurality of second pinholes are at the open configuration. Accordingly, the first projection data set may include (substantially only) photons traversing the collimator through the group of second pinholes.

In some embodiments, a second projection data set may be generated based on at least a portion of photons that traverse the collimator and are detected by the detector during the third time period when the plurality of first pinholes are at the open configuration and the plurality of second pinholes are at the blocked configuration. Accordingly, the second projection data set may include (substantially only) photons traversing the collimator through the group of first pinholes.

In some embodiments, a third projection data set may be generated based on at least a portion of photons that traverse the collimator and are detected by the detector during the fifth time period when both the plurality of first pinholes and the plurality of second pinholes are at the open configuration. Accordingly, the third projection data set may include a first portion that corresponds to photons traversing the collimator through the group of second pinholes at the open configuration and a second portion that corresponds to photons traversing the collimator through the group of first pinholes at the open configuration during the fifth time period.

In some embodiments, an image may be generated based on the first projection data set and the second projection data set. In some embodiments, the image may be generated using a reconstruction algorithm. In some embodiments, the first portion of the third projection data set and the second portion of the third projection data set may be separated based on at least one of the first projection data set, the second projection data set, or the third projection data set. The image may be further generated based on at least one of the first projection data set, the second projection data set, the first portion of the third projection data set, or the second portion of the third projection data set. In some embodiments, the image may be generated based on the first projection data set, the second projection data set, the first portion of the third projection data set, and the second portion of the third projection data set. The separation of the first portion and the second portion of the third projection data set based on the first projection data set and the second projection data set may allow image reconstruction based on at least one of the first projection data set, the second projection data set, the first portion of the third projection data set, or the second portion of the third projection data set, thereby improving the homogeneity of the image so generated.

In some embodiments, the image may be generated according to Formula (2) below:

$$\begin{bmatrix} y_{s1} \\ y_{s2} \\ y_m \end{bmatrix} = \begin{bmatrix} r_m A_1 + r_s A_2 \\ r_s A_1 + r_m A_2 \\ r_m A_1 + r_m A_2 \end{bmatrix} x \quad (2)$$

where x refers to the image, $r_s$ refers to the first transmission ratio (or the third transmission ratio equal to the first transmission ratio), $r_m$ refers to the second transmission ratio (or the fourth transmission ratio equal to the second transmission ratio), $y_{s1}$ refers to the first projection data set, $y_{s2}$ refers to the second projection data set, $y_m$ refers to the third projection data set, $A_1$ refers to a first matrix (e.g., a projection matrix) of the group of first pinholes, and $A_2$ refers to a second matrix (e.g., a projection matrix) of the group of second pinholes. As used herein, the first matrix may be used to faciliate a forward projection operation on the image through the group of first pinholes. The second matrix may be used to faciliate a forward projection operation on the image through the group of second pinholes.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A single-photon emission computed tomography (SPECT) system, comprising:
a collimator including a group of first pinholes and a group of second pinholes, wherein
the group of first pinholes are configured to remain open;
the group of second pinholes are configured to alternate between an open configuration and a blocked configuration; and
the collimator is configured to allow photons to traverse through at least one group of the group of first pinholes or the group of second pinholes, and
a detector configured to detect at least a portion of the photons that have traversed the collimator, wherein photons that traverse the collimator through each first pinhole of the group of first pinholes correspond to a first projection region on the detector, photons that traverse the collimator through each second pinhole of the group of second pinholes correspond to a second projection region on the detector; and at least one of first projection regions overlaps at least one of second projection regions.

2. The SPECT system of claim 1, wherein the SPECT system includes a plurality of filters, each of which corresponds to at least one second pinhole of the group of second pinholes.

3. The SPECT system of claim 2, wherein
for each of the plurality of filters,
the filter is movable between a first position and a second position,
when the filter is at the first position, at least one second pinhole of the group of second pinholes corresponding to the filter is at its open configuration, and
when the filter is at the second position, the at least one second pinhole corresponding to the filter is at its blocked configuration.

4. The SPECT system of claim 2, wherein
the group of second pinholes are configured to allow a first portion of the photons to traverse at the open configuration and a second portion of the photons to traverse at the blocked configuration, and
a ratio of the second portion to the first portion is smaller than a ratio threshold.

5. The SPECT system of claim 2, wherein the plurality of filters is located on a rotatable ring.

6. The SPECT system of claim 1, wherein
the group of second pinholes are configured to be at the blocked configuration during a first time period and at the open configuration during a second time period, and
the second time period is longer than the first time period.

7. The SPECT system of claim 6, wherein a switch from the blocked configuration to the open configuration of the group of second pinholes takes a third time period.

8. The SPECT system of claim 7, wherein
the third time period is smaller than at least one of the first time period or the second time period.

9. The SPECT system of claim 7, wherein a total duration of the first time period, the second time period, and the third time period is smaller than a time threshold.

10. The SPECT system of claim 1, wherein
the first projection regions are non-overlapping.

11. The SPECT system of claim 10, wherein
the second projection regions are non-overlapping.

12. The SPECT system of claim 1, wherein
at least one of the first projection regions overlaps at least two of the second projection regions; or
at least one of the second projection regions overlaps at least two of the first projection regions.

13. The SPECT system of claim 1, wherein the group of first pinholes and the group of second pinholes are alternately positioned such that each first pinhole is positioned between two neighboring second pinholes.

14. The SPECT system of claim 1, wherein the detector, the collimator, and the rotatable ring are arranged concentrically.

15. The SPECT system of claim 1, wherein a central angle between a first pinhole among the group of first pinholes and a second pinhole among the group of second pinholes that are adjacent to each other is within an angle range, and the angle range includes 1 degree~10 degrees, 2 degrees~8 degrees, or 5 degrees~6 degrees.

16. The SPECT system of claim 1, wherein at least one of an aggregate of the first projection regions or an aggregate of the second projection regions covers the entire detector.

17. A system, comprising:
a single-photon emission computed tomography (SPECT) device, the SPECT device comprising a collimator having a group of first pinholes and a group of second pinholes, wherein
the group of first pinholes are configured to remain open; and
the group of second pinholes are configured to alternate between an open configuration and a blocked configuration, wherein photons that traverse the collimator through each first pinhole of the group of first pinholes correspond to a first projection region on the detector, photons that traverse the collimator through each second pinhole of the group of second pinholes correspond to a second projection region on the detector; and at least one of first projection regions overlaps at least one of second projection regions;
at least one storage device storing executable instructions for single-photon emission computed tomography (SPECT) imaging; and
at least one processor in communication with the at least one storage device, wherein when executing the executable instructions, the at least one processor is configured to cause the system to perform operations including:
causing the group of second pinholes to maintain at the blocked configuration during a first time period;
acquiring a first projection data set during the first time period;
causing the group of second pinholes to maintain at the open configuration during a second time period;
acquiring a second projection data set during the second time period; and
generating an image based on the first projection data set and the second projection data set.

18. The system of claim 17, wherein
the second projection data set includes a first portion that corresponds to photons traversing the collimator through the group of second pinholes at the open configuration and a second portion that corresponds to photons traversing the collimator through the group of first pinholes; and
the generating an image based on the first projection data set and the second projection data set includes:
determining the first portion of the second projection data set based on the first projection data set and the second projection data set, and
generating the image based on the first projection data set and the first portion of the second projection data.

19. A single-photon emission computed tomography (SPECT) system, comprising:
a collimator including a group of first pinholes and a group of second pinholes, wherein
the group of first pinholes are configured to alternate between an open configuration and a blocked configuration;
the group of second pinholes are configured to alternate between an open configuration and a blocked configuration; and
the collimator is configured to allow photons to traverse through at least one group of the group of first pinholes or the group of second pinholes, and
a detector configured to detect at least a portion of the photons that have traversed the collimator, wherein one of a plurality of pinhole modes of the group of first pinholes and the group of second pinholes includes:
a first pinhole mode in which the group of first pinholes are configured to be at the blocked configuration, while the group of second pinholes are configured to be at the open configuration;
a second pinhole mode in which the group of first pinholes and the group of second pinholes are both configured to be at the open configuration; or
a third pinhole mode in which the group of first pinholes are configured to be at the open configuration, while the group of second pinholes are configured to be at the blocked configuration, wherein photons that traverse the collimator through each first pinhole of the group of first pinholes correspond to a first projection region on the detector, photons that traverse the collimator through each second pinhole of the group of second pinholes correspond to a second projection region on the detector; and at least one of first projection regions overlaps at least one of second projection regions.

20. The SPECT system of claim 19, further including a plurality of filters, each of which corresponds to at least one first pinhole of the group of first pinholes or at least one second pinhole of the group of second pinholes.

* * * * *